(12) United States Patent
Alonso Babarro

(10) Patent No.: US 12,318,541 B2
(45) Date of Patent: Jun. 3, 2025

(54) SHIELDED INTUBATION GUIDE AND METHOD

(71) Applicant: Airway Medical Innovations S.L., Madrid (ES)

(72) Inventor: Julio Miguel Alonso Babarro, Madrid (ES)

(73) Assignee: Airway Medical Innovations S.L., Madrid (ES)

( * ) Notice: Subject to any disclaimer, the term of this patent is extended or adjusted under 35 U.S.C. 154(b) by 422 days.

(21) Appl. No.: 17/621,608

(22) PCT Filed: Jun. 24, 2020

(86) PCT No.: PCT/AU2020/050639
§ 371 (c)(1),
(2) Date: Dec. 21, 2021

(87) PCT Pub. No.: WO2020/257851
PCT Pub. Date: Dec. 30, 2020

(65) Prior Publication Data
US 2022/0355052 A1    Nov. 10, 2022

(30) Foreign Application Priority Data
Jun. 24, 2019    (AU) .................... 2019902197

(51) Int. Cl.
*A61B 1/00*    (2006.01)
*A61B 1/267*    (2006.01)
*A61M 16/04*    (2006.01)

(52) U.S. Cl.
CPC ....... *A61M 16/047* (2013.01); *A61B 1/00048* (2013.01); *A61B 1/267* (2013.01);
(Continued)

(58) Field of Classification Search
CPC .............. A61M 16/047; A61M 16/049; A61M 16/0495; A61M 16/0463; A61M 16/04; A61B 1/00048; A61B 1/267
(Continued)

(56) References Cited

U.S. PATENT DOCUMENTS

| 4,848,331 A | 7/1989 | Northway-Meyer |
| 6,244,865 B1 | 6/2001 | Nelson et al. |

(Continued)

FOREIGN PATENT DOCUMENTS

| WO | WO 2001091838 | 12/2001 |
| WO | WO 2016090435 | 6/2016 |

(Continued)

OTHER PUBLICATIONS

International Preliminary Report on Patentability in International Appln. No. PCT/AU2020/050639, dated Dec. 28, 2021, 10 pages.
(Continued)

*Primary Examiner* — Timothy J Neal
*Assistant Examiner* — James Edward Boice
(74) *Attorney, Agent, or Firm* — Fish & Richardson P.C.

(57) ABSTRACT

A shielded intubation guide for use in an endotracheal intubation procedure, the shielded intubation guide including: an elongate body defining a passageway extending between a proximal opening and a distal opening for receiving a blade portion of an intubation device, the shielded intubation guide being configured for insertion into a mouth of the subject so that the proximal opening is positioned proximate to the mouth and the distal opening is positioned in an airway of the subject; and a shield around the proximal opening for substantially reducing emissions from the mouth, the shielded intubation guide allowing endotracheal intubation to be performed by: inserting the blade portion of the intubation device into the passageway; positioning a
(Continued)

distal end of the blade portion proximate to the larynx of the subject; and advancing an endotracheal tube along the blade portion through the passageway into a trachea of the subject.

25 Claims, 18 Drawing Sheets

(52) U.S. Cl.
CPC ...... *A61M 16/0463* (2013.01); *A61M 16/049* (2014.02); *A61M 16/0495* (2014.02)

(58) Field of Classification Search
USPC .......................................... 600/120, 121, 185
See application file for complete search history.

(56) References Cited

U.S. PATENT DOCUMENTS

| | | | |
|---|---|---|---|
| 2002/0033175 A1* | 3/2002 | Bateman | A61M 16/049 128/206.29 |
| 2007/0197876 A1 | 8/2007 | Lane | |
| 2008/0230055 A1* | 9/2008 | NaPier | A61M 16/0497 128/200.26 |
| 2010/0132700 A1 | 6/2010 | Filipi et al. | |
| 2010/0191062 A1 | 7/2010 | Kieffer | |
| 2010/0249513 A1* | 9/2010 | Tydlaska | A61B 1/00052 248/219.4 |
| 2012/0172740 A1* | 7/2012 | Hu | A61M 16/06 128/206.21 |
| 2013/0197303 A1* | 8/2013 | Chun | A61M 16/06 600/103 |
| 2015/0112146 A1* | 4/2015 | Donaldson | A61B 1/00048 600/188 |
| 2015/0283344 A1 | 10/2015 | Olympio | |
| 2016/0199609 A1* | 7/2016 | Gulka | A61M 15/0021 128/200.14 |
| 2017/0319462 A1* | 11/2017 | Marchant | A61K 8/64 |

FOREIGN PATENT DOCUMENTS

| | | |
|---|---|---|
| WO | WO 2017068221 A1 | 4/2017 |
| WO | WO 2020000031 | 1/2020 |

OTHER PUBLICATIONS

International Search Report and Written Opinion in International Appln. No. PCT/AU2020/050639, dated Aug. 10, 2020, 14 pages.

* cited by examiner

SHIELDED INTUBATION GUIDE AND METHOD

BACKGROUND OF THE INVENTION

The present invention relates to a shielded intubation guide and a method for use in an endotracheal intubation procedure, being particularly adapted to allow endotracheal intubation of a subject whilst substantially reducing emissions from the mouth of the subject during the procedure.

DESCRIPTION OF THE PRIOR ART

Endotracheal intubation is the procedure through which a medical professional introduces a flexible plastic conduit, an endotracheal tube, generally through the mouth and into the trachea. This allows artificial ventilation, which is required when the breathing ability is compromised by an illness or injury in an emergency situation or is interfered by drug-induced depression during surgery. It is a universal procedure and is performed in the same fashion all over the world.

Every day thousands of intubations are performed by a diverse range of professionals, particularly anaesthetics specialists, intensivists, emergency physicians and pre-hospital medics and paramedics. However endotracheal intubation is a high risk procedure which can lead to death or disability, requires considerable skill and occasionally cannot be accomplished. Even to highly trained professionals, it is often difficult and sometimes unsuccessful. New specialised instruments and advanced techniques are continuously developing with the aim to facilitate this difficult procedure and ensure better success rates.

The aim of the operator is to successfully pass an endotracheal tube through the mouth, pharynx and larynx and into the trachea. The oropharyngeal passage is curved and narrow and ends at the entrance of both the larynx and the oesophagus. The tongue tends to fall back on to the pharynx when a patient is in supine position, the entrance of the larynx can vary in its position due to the particular anatomy of a patient and the epiglottis lies over the entrance of the larynx and usually needs to be moved to expose the glottic opening.

The operator needs to identify the vocal cords at the entrance of the larynx, the epiglottis above the entrance of the larynx in the transversal view with the patient supine, and the oesophagus, below all previous structures on this view. This procedure requires extraordinary skills; it is easier for the endotracheal tube to follow the path towards the oesophagus, it is often difficult to obtain a good view of the larynx, and even with a good view, it is difficult sometimes to introduce the endotracheal tube. Any delay in successfully finalising the procedure is a serious complication, and may potentially be fatal.

The insertion of an endotracheal tube through all these anatomical structures and into the trachea is referred to as endotracheal intubation and typically requires the use of an instrument called laryngoscope which comprises a handle, and a blade. Different shapes of the blade may be used depending on a range of factors such as the age or size of the patient and different procedural options. Laryngoscope blades are generally classified as curved or straight, although a number of styles of curved and straight blades are commercially available. Some styles of blades are designed to be positioned anterior to the epiglottis, and other styles are designed to be positioned posterior to the epiglottis, leading to slightly different movements during the procedure. A light source may be provided at the tip of the blade to illuminate the area beyond. The light source may be powered by batteries within the handle.

During endotracheal intubation, generally with the patient laying supine, the operator, standing at the top of the head of the patient, introduces the blade of the laryngoscope through the mouth and into the pharynx and manipulates anatomical structures such as the tongue and the epiglottis (depending on the particular patient and type of blade) to expose the entrance of the larynx. Then, under direct visualisation, the operator inserts the tip of the endotracheal tube into the larynx and advances it into the trachea. In the conventional and universal procedure, the operator typically utilises the left hand to hold the laryngoscope by the handle to position the blade and utilises the right hand to carefully introduce the endotracheal tube, pushing it alongside the laryngoscope blade and into the visualised trachea.

Often, because of anatomical variations and challenges, and despite an adequate technique, direct visualisation is difficult. In most of these occasions, adequate visualisation could be obtained by manipulating some of the anatomical structures. Unfortunately, with the conventional laryngoscope and conventional procedure, the operator is utilising both hands and the hand being used to manually introduce the endotracheal tube cannot be used to manipulate anatomical structures to facilitate the procedure. Furthermore, a second operator could not have direct visual access to the entrance of the larynx to help manipulating these structures and will interfere with the vision of the first operator, as the mouth opening, through which the first operator is obtaining the view, is very limited and the operator performing the intubation procedure will usually be in the best viewing position. Video laryngoscopes are available to remove the need for a direct view, although these are typically bulkier than conventional laryngoscopes and still occupy both hands of the operator.

Due to the degree of difficulty of the procedure itself, together with the seriousness of the potential complications, this procedure will only be performed by highly skilled professionals. This difficulty and serious complication risk have also meant that the procedure, and the instruments used to perform it, has essentially remained unchanged for decades. The physicians and other professionals who perform endotracheal intubations are unwilling to use new devices or to change the way this is conventionally done, given the difficulties and risks. A new intubation device therefore not only has to offer obvious procedural advantages in comparison to the conventional laryngoscopes, but also has to present similar characteristics in shape and weight and in its method of use, to facilitate adoption by operators already trained and comfortable in the use of conventional laryngoscopes in the often stressful circumstances of performing an intubation procedure.

WO/2016/090435A1 discloses a new intubation device that allows an endotracheal intubation procedure to be performed using a single hand. In particular, the intubation device includes: a laryngoscope blade having a tip and a base; a handle attached to the base of the blade for allowing the intubation device to be held in a hand of a user; a channel for receiving an endotracheal tube, the channel including a blade channel portion extending along the blade substantially from the tip to the base and including an outlet proximate to the tip for allowing a distal end of the endotracheal tube to be advanced from the outlet and a handle channel portion extending partially along the handle from the blade channel portion; and a tube movement mechanism in the handle for moving the endotracheal tube through the channel to thereby advance the endotracheal tube, the tube movement mechanism including a thumb interface for allowing the user to operate the tube movement mechanism using a thumb of the hand that is holding the intubation device, to thereby allow the user to hold the intubation device and advance the endotracheal tube in an endotracheal intubation procedure using a single hand. The entire contents of WO/2016/090435A1 are incorporated herein by reference.

By enabling single handed operation of the intubation device for positioning the blade via the handle and advancing the endotracheal tube, the other hand of the user will remain free for other uses, such as clearing the airway using another device, such as a suction device, or other devices such as forceps or the like to manipulate anatomical structures and/or the endotracheal tube, during the endotracheal intubation procedure as may be required.

During an endotracheal intubation procedure, emissions from the mouth of the subject can be problematic. For example, emissions of fluids, droplets or aerosols from the subject's mouth during the procedure may expose the user of the intubation device or other medical staff in the vicinity to infectious diseases. In particular, the risk of viral transmission via fluids, droplets and/or aerosols emitted from the mouth has been of increased concern during the COVID-19 pandemic. The risk of exposure to the user will be especially elevated due to the user's close proximity to the subject's mouth and the increased likelihood of the subject coughing or gagging during the procedure.

It would therefore be desirable to provide a device and method to allow endotracheal intubation of a subject whilst substantially reducing emissions from the mouth of the subject during the procedure, ideally using an intubation device similar to those already routinely used by medical practitioners.

To assist in visualisation, laryngoscopes and other forms of intubation devices may include a light source near the tip of the blade, for providing illumination during the procedure and thus improving the visibility of anatomical features in the vicinity of the larynx. Such a light source can be useful for direct visualisation using conventional laryngoscopes, or for non-direct visualisation using video laryngoscopes or the like. When an endotracheal intubation procedure is performed using a light source it may be referred to as light guided endotracheal intubation.

Light guided endotracheal intubation can be of assistance in most scenarios, but may be essential when intubation needs to be performed in darkness or in poor lighting conditions. However, the use of light guided endotracheal intubation may be problematic in some situations where the escape of light from the subject's mouth is undesirable. For instance, if military doctors or medics perform light guided endotracheal intubations in dark conditions during combat, light escaping from the subject's mouth would present an open light source, which could reveal their location to the enemy and make them a target.

In situations where the escape of light from the subject's mouth is problematic, it may be desirable to provide a device and method to allow light guided endotracheal intubation of a subject whilst substantially preventing light from escaping from the mouth of the subject during the procedure, ideally using an intubation device similar to those already routinely used by medical practitioners.

The reference in this specification to any prior publication (or information derived from it), or to any matter which is known, is not, and should not be taken as an acknowledgment or admission or any form of suggestion that the prior publication (or information derived from it) or known matter forms part of the common general knowledge in the field of endeavour to which this specification relates.

SUMMARY OF THE PRESENT INVENTION

In one broad form, an aspect of the present invention seeks to provide a shielded intubation guide for use in an endotracheal intubation procedure, the shielded intubation guide including: an elongate body defining a passageway extending between a proximal opening and a distal opening, the passageway being configured for receiving a blade portion of an intubation device, wherein the shielded intubation guide is configured for insertion into a mouth of the subject so that the proximal opening is positioned proximate to the mouth of the subject and the distal opening is positioned in an airway of the subject; and a shield around the proximal opening, wherein the shield is configured to substantially reduce emissions from the mouth of the subject, wherein the shielded intubation guide is configured to allow endotracheal intubation of the subject to be performed using an intubation device and the shielded intubation guide by: inserting the blade portion of the intubation device into the passageway of the shielded intubation guide; positioning a distal end of the blade portion of the intubation device proximate to the larynx of the subject; and advancing an endotracheal tube along the blade portion of the intubation device through the passageway into a trachea of the subject.

In one embodiment, the shield is configured to substantially reduce emissions from the mouth of the subject of one or more of: fluids; droplets; aerosols; and light emitted from a light source proximate to the distal end of the blade portion of the intubation device during a light guided endotracheal intubation procedure.

In one embodiment, the shield is configured to substantially cover the mouth of the subject in use.

In one embodiment, the shield includes a flange extending outwardly from the body, the flange being configured to substantially cover the mouth of the subject in use.

In one embodiment, the flange surrounds the proximal opening.

In one embodiment, the flange includes opposing lateral flange portions that are curved towards the distal opening.

In one embodiment, the flange includes a superior edge having a recess for aligning with a nose of the subject in use.

In one embodiment, the flange is configured to prevent over-insertion of the shielded intubation guide by abutting the subject's mouth to thereby ensure that the proximal opening remains positioned outside the mouth.

In one embodiment, the proximal opening is at least one of: offset proximally from the flange; and oriented at an angle relative to the flange.

In one embodiment, the shielded intubation guide is configured to be broken along the passageway and along a section of the shield.

In one embodiment, the body of the shielded intubation guide includes a break line extending longitudinally along a side of the passageway and along the section of the shield, to thereby allow the shielded intubation guide to be broken along the break line.

In one embodiment, the break line is defined along a central plane of the shielded intubation guide.

In one embodiment, the shielded intubation guide includes cutting marks and is configured to be cut along the passageway and along a section of the shield, by following the cutting marks.

In one embodiment, a shape of the proximal opening is selected based on a cross section shape of the blade portion of the intubation device.

In one embodiment, a size of the proximal opening is selected based on a cross section size of the blade portion of the intubation device.

In one embodiment, a shape of the passageway is selected based on a cross section shape of the blade portion of the intubation device.

In one embodiment, a size of the passageway is selected based on a cross section size of the blade portion of the intubation device.

In one embodiment, the shielded intubation guide is formed from a flexible material.

In one embodiment, the shielded intubation guide is configured to expand when receiving the blade portion.

In one embodiment, at least one wall of the body includes an expandable region.

In one embodiment, the expandable region at least one of: extends longitudinally from the distal opening at least partially along the passageway and allows the body to expand circumferentially; and extends circumferentially around the body and allows the body to expand longitudinally.

In one embodiment, the body is curved.

In one embodiment, a curvature of the body is selected based on a curvature of the blade portion of the intubation device.

In one embodiment, the shielded intubation guide includes a seal covering the proximal opening, the seal normally being in a closed position for sealing the proximal opening and being moveable to an open position when the blade portion of the intubation device is inserted through the passageway.

In one embodiment, the seal is biased towards the closed position, such that the seal returns towards the closed position when the blade portion of the intubation device is removed from the passageway.

In one embodiment, the seal is configured to form a partial seal surrounding at least one of the blade portion of the intubation device and the endotracheal tube in use.

In one embodiment, the shielded intubation guide includes a removable cap for closing the proximal opening when the blade portion of the intubation device is not being inserted into the passageway of the shielded intubation guide.

In one embodiment, the cap includes a seal for covering the proximal opening, the seal normally being in a closed position for sealing the proximal opening and being moveable to an open position when the blade portion of the intubation device is inserted through the passageway.

In one embodiment, the shielded intubation guide is configured to, in use, at least one of: hold a tongue of the subject; and depress the tongue.

In one embodiment, the shielded intubation guide is configured to allow ventilation of the subject using a ventilation mask and ventilator prior to endotracheal intubation being performed.

In one embodiment, the shielded intubation guide is configured for use in a light guided endotracheal intubation procedure in which, after the blade portion of the intubation device is inserted into the passageway of the shielded intubation guide, light is emitted from a light source proximate to the distal end of the blade portion of the intubation device, wherein the shield is configured to substantially prevent light emitted from the light source from escaping from the mouth of the subject.

In one embodiment, at least one of: the light shield is formed from an opaque material; and the entire shielded intubation guide is formed from an opaque material.

In one embodiment, the shielded intubation guide is formed from a transparent material.

In one embodiment, the shield includes a rim that is configured to engage with a face of the subject to thereby form a seal around the mouth of the subject.

In one embodiment, the body has a length selected so that the distal opening is positioned in one of: proximate to an oral cavity of the subject; proximate to a pharynx of the subject; and between a tongue and a palate of the subject.

In one embodiment, the shielded intubation guide includes at least one additional opening extending through the shield for facilitating access to an oral cavity of the subject.

In one embodiment, the shielded intubation guide includes at least one suction port extending through the shield.

In one embodiment, the shielded intubation guide includes at least one drainage conduit extending through the shield.

In another broad form, an aspect of the present invention seeks to provide a method for use in an endotracheal intubation procedure, the method including: inserting a shielded intubation guide into a mouth of a subject, the shielded intubation guide including: an elongate body defining a passageway extending between a proximal opening and a distal opening, the passageway being configured for receiving a blade portion of an intubation device, the proximal opening being positioned proximate to the mouth of the subject and the distal opening being positioned in an airway of the subject; and a shield around the proximal opening, the shield being for substantially reducing emissions from the mouth of the subject; performing endotracheal intubation of the subject using an intubation device and the shielded intubation guide by: inserting the blade portion of the intubation device into the passageway of the shielded intubation guide; positioning a distal end of the blade portion of the intubation device proximate to the larynx of the subject; and advancing an endotracheal tube along the blade portion of the intubation device through the passageway into a trachea of the subject, wherein the shield substantially reduces emissions from the mouth of the subject during the endotracheal intubation procedure.

In one embodiment, the shield substantially reduces emissions from the mouth of the subject of one or more of: fluids; droplets; aerosols; and light emitted from a light source proximate to the distal end of the blade portion of the intubation device during a light guided endotracheal intubation procedure.

In one embodiment, the method includes performing light guided endotracheal intubation of the subject using an intubation device and the shielded intubation guide by, after inserting the blade portion of the intubation device into the passageway of the intubation guide, causing light to be emitted from a light source proximate to the distal end of the blade portion of the intubation device, wherein the shield substantially prevents light emitted from the light source from escaping from the mouth of the subject during the light guided endotracheal intubation procedure.

In one embodiment, the endotracheal intubation is performed as non-direct view intubation.

In one embodiment, the intubation device includes a video camera located proximate to the tip of the blade, the method including: causing images captured by the video camera to be presented to a user on a display; and the user performing the endotracheal intubation of the subject with reference to the images presented on the display.

In one embodiment, the display is integrated with the intubation device.

In one embodiment, the display is provided in the form of goggles worn by the user.

In one embodiment, the display is surrounded by display light shielding configured so that the user can view the display whilst the display light shielding substantially prevents light emitted from the display from escaping beyond the display light shielding and the user's face.

In one embodiment, the shield substantially covers the mouth of the subject when the shielded intubation guide is inserted into the mouth of the subject.

In one embodiment, the shield includes a flange extending outwardly from the body, and wherein the flange substantially covers the mouth of the subject when the shielded intubation guide is inserted into the mouth of the subject.

In one embodiment, the method includes, after advancing the endotracheal tube into the trachea of the subject, and while leaving the endotracheal tube in place in the trachea of the subject: withdrawing the blade portion of the intubation device from the shielded intubation guide; and removing the shielded intubation guide from the mouth of the subject.

In one embodiment, the shielded intubation guide is configured to be broken along the passageway and along a section of the shield, the method including breaking the shielded intubation guide to allow the shielded intubation guide to be removed while the endotracheal tube remains in place.

In one embodiment, the method includes cutting the shielded intubation guide along the passageway and along a section of the shield to allow the shielded intubation guide to be removed while the endotracheal tube remains in place.

In one embodiment, the method includes, prior to endotracheal intubation being performed, ventilating the subject using a ventilation mask and ventilator.

In one embodiment, the shielded intubation guide includes a seal covering the proximal opening, the seal normally being in a closed position for sealing the proximal opening and being moveable to an open position when the blade portion of the intubation device is inserted through the passageway, the method including inserting the blade portion of the intubation device into the passageway of the shielded intubation guide through the seal, the seal substantially reducing emissions from the mouth at least prior to inserting the blade.

In one embodiment, the seal is biased towards the closed position, such that the seal returns towards the closed position when the blade portion of the intubation device is removed from the passageway, the seal forming a partial seal surrounding at least one of the blade portion of the intubation device and the endotracheal tube after inserting the blade.

In one embodiment, the shielded intubation guide includes a removable cap for sealing the proximal opening, the method including: inserting the shielded intubation guide into the mouth of a subject with the cap sealing the proximal opening, thereby substantially reducing emissions from the mouth of the subject through the proximal opening while the cap is in place; and, removing the cap prior to inserting the blade portion of the intubation device into the passageway of the shielded intubation guide.

In one embodiment, the shielded intubation guide includes at least one suction port extending through the shield, the method including performing suction of fluids from an oral cavity of the subject via the suction port.

In one embodiment, the shielded intubation guide includes at least one drainage conduit extending through the shield, the method including allowing fluids to drain from an oral cavity of the subject via the drainage conduit.

In another broad form, an aspect of the present invention seeks to provide a light shielded intubation guide for use in an endotracheal intubation procedure, the light shielded intubation guide including: an elongate body defining a passageway extending between a proximal opening and a distal opening, the passageway being configured for receiving a blade portion of an intubation device; and a light shield near the proximal opening, wherein the light shielded intubation guide is configured for insertion into a mouth of the subject so that the proximal opening is positioned proximate to the mouth of the subject and the distal opening is positioned proximate to a pharynx of the subject, to thereby allow light guided endotracheal intubation of the subject to be performed using an intubation device and the light shielded intubation guide by: inserting the blade portion of the intubation device into the passageway of the light shielded intubation guide; causing light to be emitted from a light source proximate to the distal end of the blade portion of the intubation device, wherein the light shield is configured to substantially prevent light emitted from the light source from escaping from the mouth of the subject; positioning a distal end of the blade portion of the intubation device proximate to the larynx of the subject; and advancing an endotracheal tube along the blade portion of the intubation device through the passageway into a trachea of the subject.

In another broad form, an aspect of the present invention seeks to provide a method for use in an endotracheal intubation procedure, the method including: inserting a light shielded intubation guide into a mouth of a subject, the light shielded intubation guide including: an elongate body defining a passageway extending between a proximal opening and a distal opening, the passageway being configured for receiving a blade portion of an intubation device, the proximal opening being positioned proximate to the mouth of the subject and the distal opening being positioned proximate to a pharynx of the subject; and a light shield near the proximal opening, the light shield being for substantially preventing light from escaping from the mouth of the subject; performing light guided endotracheal intubation of the subject using an intubation device and the light shielded intubation guide by: inserting the blade portion of the intubation device into the passageway of the light shielded intubation guide; causing light to be emitted from a light source proximate to the distal end of the blade portion of the intubation device, wherein the light shield substantially prevents light emitted from the light source from escaping from the mouth of the subject; positioning a distal end of the blade portion of the intubation device proximate to the larynx of the subject; and advancing an endotracheal tube along the blade portion of the intubation device through the passageway into a trachea of the subject.

It will be appreciated that the broad forms of the invention and their respective features can be used in conjunction, interchangeably and/or independently, and reference to separate broad forms is not intended to be limiting.

BRIEF DESCRIPTION OF THE DRAWINGS

Various examples and embodiments of the present invention will now be described with reference to the accompanying drawings, in which:—

DETAILED DESCRIPTION OF THE PREFERRED EMBODIMENTS

An example of a shielded intubation guide for use in performing an endotracheal intubation procedure on a subject 100 will now be described with reference to FIGS. 1A to 1H, showing the shielded intubation guide 110 in use in different steps of the procedure, and FIGS. 2A to 2D, showing further details of the shielded intubation guide 110.

The shielded intubation guide 110 is particularly adapted to allow endotracheal intubation to be performed using a bladed intubation device 140 (as shown in FIGS. 1C to 1F), such as a laryngoscope or the like. For the purpose of the following examples, it is assumed that the intubation device 140 is a single handed intubation device as described in WO/2016/090435A1, although it should be appreciated that other forms of intubation devices may be used with appropriate adaptations to the shielded intubation guide 110. For example, embodiments of the shielded intubation guide 110 may be configured for use with commercially available video laryngoscopes or conventional, direct vision laryngoscopes.

Figure 1A:
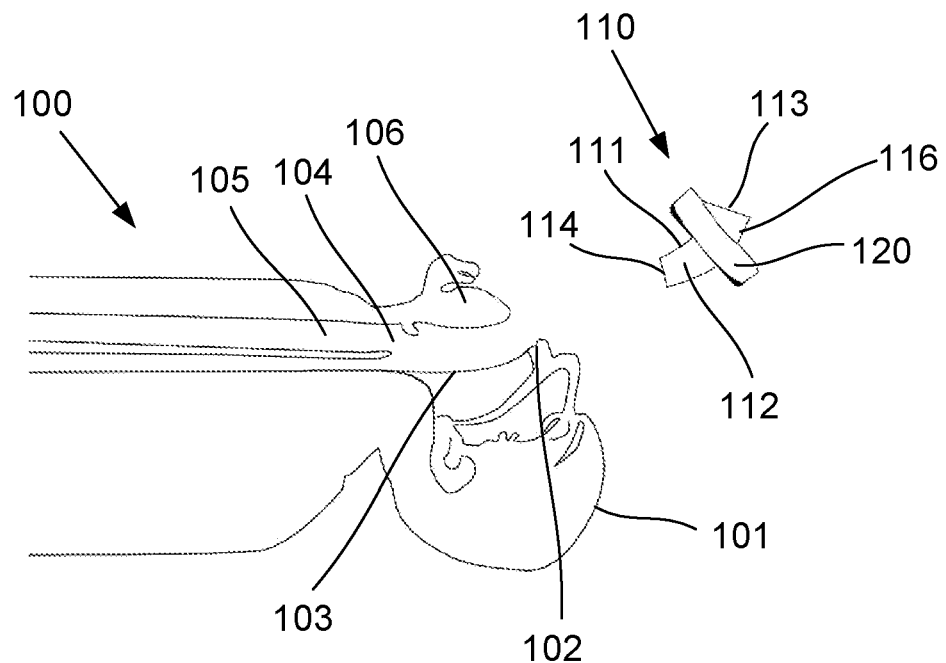
FIGS. 1A to 1H are cross section views showing steps of an endotracheal intubation procedure being performed on a subject using a first example of a shielded intubation guide.

In broad terms, and with regard to FIG. 1A, the shielded intubation guide 110 includes an elongate body 111 defining a passageway 112 extending between a proximal opening 113 and a distal opening 114. The passageway 112 of the shielded intubation guide 110 is configured for receiving a blade portion 142 of an intubation device 140, as shown in FIGS. 1D to 1F, and in further detail in FIGS. 3A and 3B. The shielded intubation guide 110 also includes a shield 120 positioned near the proximal opening 114.

Figure 1B:
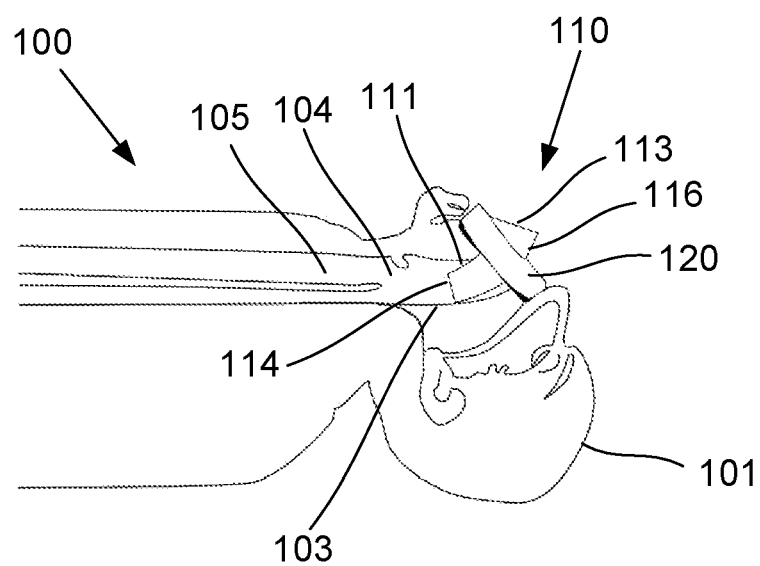

The shielded intubation guide 110 is specifically configured for insertion into a mouth 102 of the subject 100, as shown in FIG. 1B, so that the proximal opening 113 is positioned proximate to the mouth 102 of the subject 100 and the distal opening 114 is positioned in an airway of the subject.

Different embodiments of the shielded intubation guide 110 may be configured for positioning the distal opening 114 in different anatomical regions of the subject. For example, the body 111 of the shielded intubation guide 110 may have a length selected so that the distal opening 114 is positioned proximate to an oral cavity of the subject or proximate to a pharynx of the subject. In some examples, the distal opening 114 may be positioned between a tongue and a palate of the subject, whilst in other examples, the distal opening 114 may be positioned behind the tongue in the oro-pharynx if the subject.

The shield 120, which is positioned around the proximal opening 113, will be positioned proximate to the mouth 102 of the subject 100. The shield 120 is configured to substantially reduce emissions from the mouth 102 of the subject 100. Further details of the shield 120 can be seen in FIGS. 2A to 2D and these will be described in due course. Typically, the shield 120 is configured to substantially cover the mouth of the subject in use, and may include a flange extending outwardly from the body 111, where the flange substantially covers the mouth 102 of the subject 100 in use.

With the shielded intubation guide 110 inserted into the mouth 102 of the subject 100, this will allow endotracheal intubation of the subject 100 to be performed using the intubation device 140 and the shielded intubation guide 110. A detailed example of a method for use in an endotracheal intubation procedure, using the shielded intubation guide 110, will be described in due course with further reference to FIGS. 1A to 1H. However, in the context of describing the configuration of the shielded intubation guide 110, an endotracheal intubation procedure is performed using the shielded intubation guide 110 by: inserting the blade portion 142 of the intubation device 140 into the passageway 112 of the shielded intubation guide 110 (as shown in FIG. 1D); positioning a distal end 143 of the blade portion 142 of the intubation device 140 proximate to the larynx 104 of the subject 100 (as also shown in FIG. 1D); and advancing an endotracheal tube 150 along the blade portion 142 of the intubation device 140 through the passageway 112 into a trachea 105 of the subject (as shown in FIG. 1F).

In any event, it will be appreciated that the shielded intubation guide 110 can be used to substantially reduce emissions from the mouth of the subject in use, both before and during the procedure. For instance, the shield 120 may be configured to substantially reduce emissions of fluids, droplets and/or aerosols from the subject's mouth 102, and as such, may be used to limit exposure of the user of the intubation device 140, or other medical staff in the vicinity of the subject, to infectious diseases that may otherwise be transmitted from the subject via these emissions from the subject's mouth. Alternatively or additionally, the shield 120 may be configured to substantially reduce emissions from the subject's mouth 102 of light emitted from a light source proximate to the distal end of the blade portion of the intubation device during a light guided endotracheal intubation procedure, in scenarios where light escaping from the mouth of the subject may be undesirable.

An example of a method for use in an endotracheal intubation procedure, using the shielded intubation guide 110 as described above, will now be described in further detail with reference to FIGS. 1A to 1H.

With reference to FIG. 1A, the method commences with the subject 100 lying in a supine position, in a similar manner as per a conventional endotracheal intubation procedure. The subject's head 101 may be tilted, to adjust the relative positioning of the subject's mouth 102, pharynx 103 and larynx 104 to better facilitate access to the larynx during the procedure.

At FIG. 1A, the shielded intubation guide 110 is provided for insertion into the mouth 102 of the subject 100.

The shielded intubation guide 110 is then inserted into the mouth 102 of the subject 100 as shown in FIG. 1B. When the shielded intubation guide 110 has been properly inserted, the proximal opening 113 will be positioned proximate to the mouth 102 of the subject 100 and the distal opening 114 will be positioned in the airway of the subject 100. In this example, the distal opening 114 is positioned proximate to a pharynx 103, but as discussed above, the position of the distal opening 114 will depend on a length of the body 111 and in other examples, the distal opening 114 may be positioned in the oral cavity, for instance between the tongue 106 and the palate of the subject 100. The shield 120, which is positioned around the proximal opening 114, will also be positioned proximate to the mouth 102 of the subject 100, for substantially reducing emissions from the mouth of the subject.

Typically the proximal opening 113 and the shield 120 will both be located outside of the mouth 102 of the subject 100, such that the shield 120 substantially covers the mouth 102, but this is not essential and it will be appreciated that alternative designs may include one or both of the shield 120 and the proximal opening 113 being at least partially inside the mouth 102. However, in the present embodiment, the shield 120 includes a flange that surrounds the body 111 and covers the outside of the mouth 102, and the body 111 includes a protruding portion 116 that protrudes proximally from the shield 120 such that the proximal opening 113 is located outside of the mouth 102.

Figure 1C:
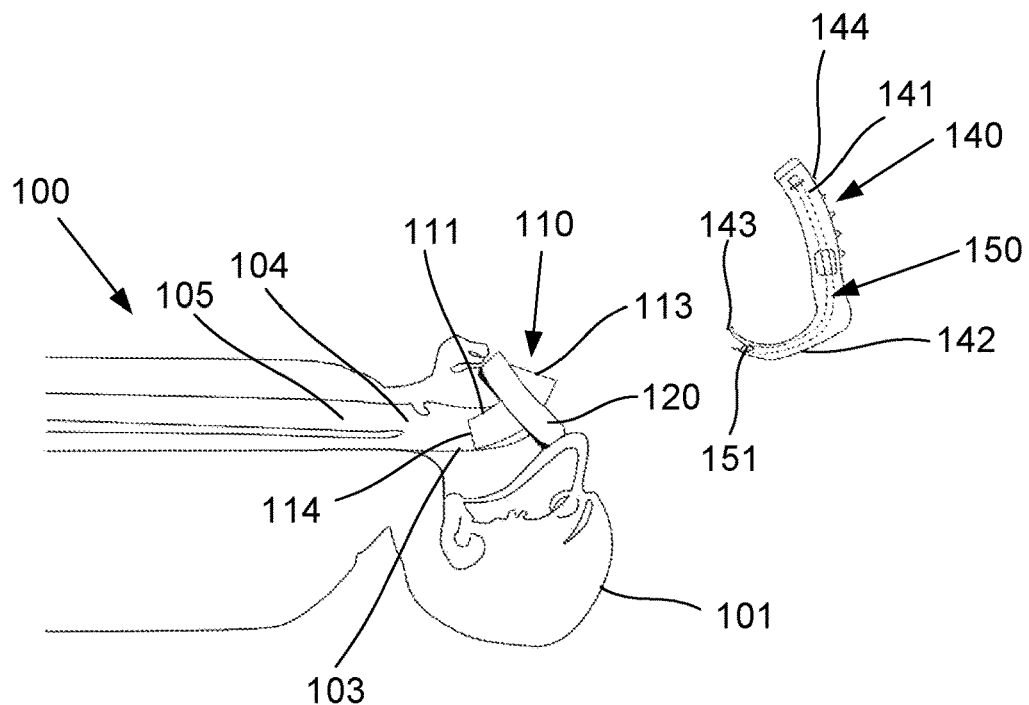
Figure 1D:
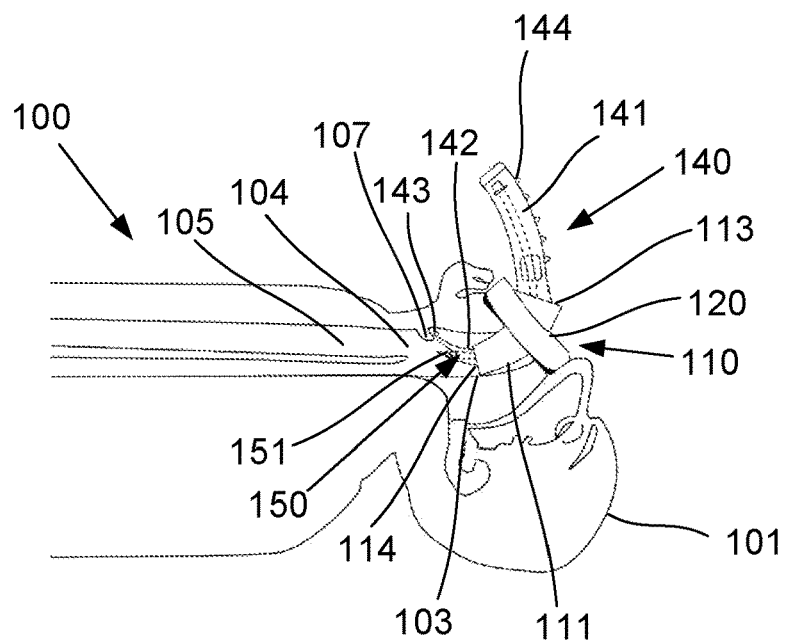
Figure 1E:
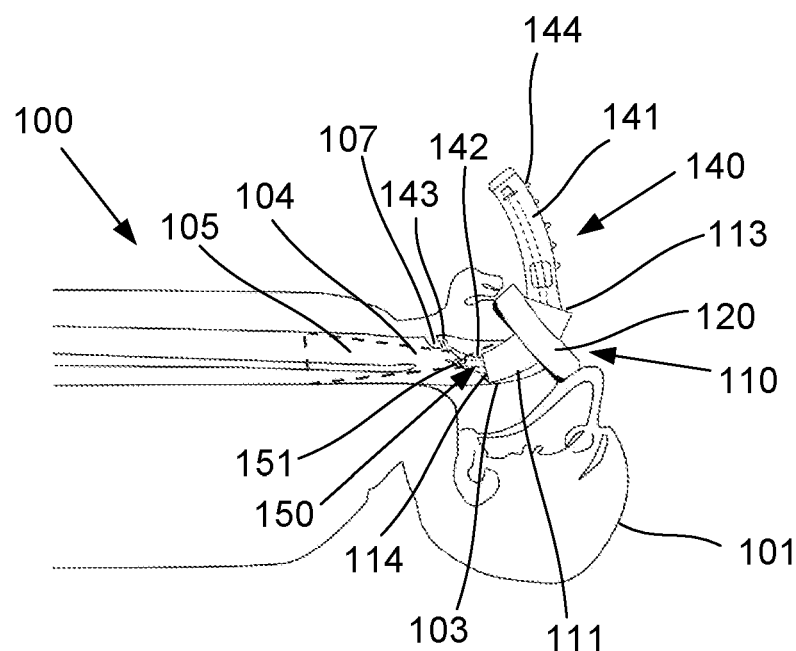
Figure 1F:
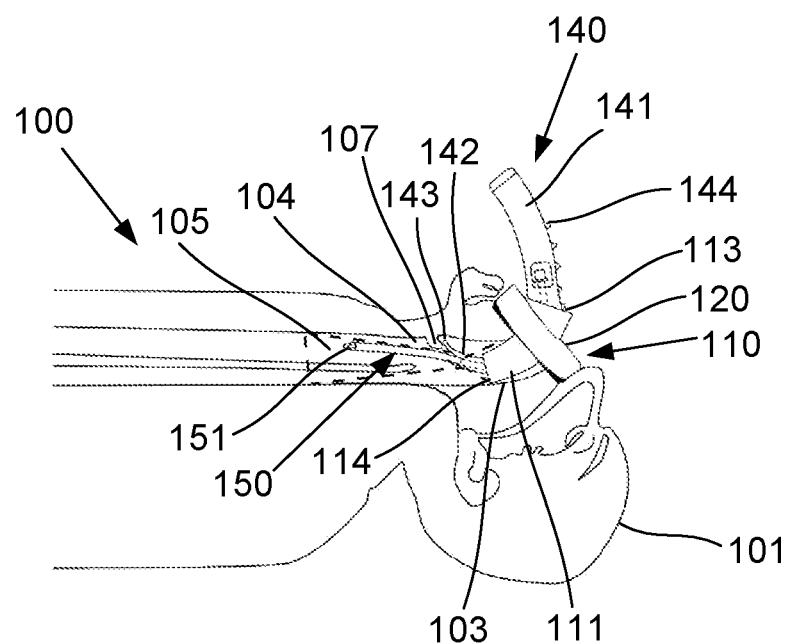

Turning to FIG. 1C, once the shielded intubation guide 110 has been inserted, an intubation device 140 will be provided for performing endotracheal intubation of the subject 100.

As mentioned above, in this example the intubation device 140 is a single handed intubation device and includes a handle portion 141 connected to the blade portion 142, for allowing the user to hold the intubation device 140 and move the blade portion 142 and the distal tip 143 relative to the subject's anatomy. This form of intubation device 140 includes a channel for receiving an endotracheal tube 150, and a tube movement mechanism in the handle portion 141 for moving the endotracheal tube 150 through the channel to thereby advance the endotracheal tube 150. In this case, the tube movement mechanism includes a thumb interface 144 for allowing the user to operate the tube movement mechanism using a thumb of the hand that is holding the intubation device, to thereby allow the user to hold the intubation device 140 and advance the endotracheal tube 150 in an endotracheal intubation procedure using a single hand.

The intubation device 140 will typically include a light source (not shown) located proximate to the distal end of the blade portion 142, for providing illumination during the endotracheal intubation procedure, in which case the procedure may be referred to as light guided endotracheal intubation. It will be noted that, in practice, most endotracheal intubation procedures will typically be performed as light guided endotracheal intubation procedures and so the terms will be used interchangeably herein.

As mentioned above, embodiments of the shielded intubation guide 110 may be configured to substantially reduce emission of light from the subject's mouth while a light guided endotracheal intubation procedure is being performed. In this case, the shield 120 of the shielded intubation guide 110 will effectively act as a light shield, which may be used to substantially prevent light emitted from the light source from escaping from the mouth of the subject during the light guided endotracheal intubation procedure. Further details of such a scenario will be described in due course.

It should be understood, that this light shielding functionality may only be required in particular scenarios where the escape of light from the mouth may be undesirable, such as in dark conditions in military settings, where light escaping from the subject's mouth would present an open light source, which could reveal their location to the enemy and make them a target. However, in many other scenarios, the escape of light will not be a problem and the shielded intubation guide 110 will not necessarily require this light shielding functionality. In any event, it will generally be desirable for the shield to substantially reduce other emissions from the mouth of the subject, irrespective of whether light guided endotracheal intubation is being performed and whether light shielding is required.

The intubation device 140 may be configured to allow light guided endotracheal intubation to be performed as non-direct view intubation, that is to say the user can perform the procedure without a direct line-of-sight visualisation of the larynx 104 and nearby anatomy of the subject 100 while inserting the blade portion 142 of the intubation device 140.

In some examples, the intubation device 140 may further include a fiber optic viewing arrangement (not shown) for allowing the user to observe anatomical structures inside the patient without requiring a direct view. The fiber optic viewing arrangement may include a flexible fiber optic bundle with a lens positioned at one end proximate to the distal tip 143 of the blade portion 142 and an eyepiece positioned at the other end. The fiber optic bundle may run along the blade portion 142 and into the handle portion 141. The eyepiece may be located on the handle portion 141 or on a suitably formed projection from the handle portion 141 to allow the user to look into the eyepiece during the procedure.

In other examples, the intubation device 140 may include a video camera (not shown) located proximate to the distal tip 143 of the blade portion 142, for providing video imaging of anatomical structures inside the patient during the procedure. It will be appreciated that this can provide even more flexible viewing options compared to the fiber optic viewing arrangement discussed above.

The video camera may be connected to a display (not shown) for presenting images from the video camera in real-time or near real-time during the procedure. Whilst a small display may be integrated with the intubation device 142, it may be preferable to provide a separate, larger display for displaying magnified images of the internal anatomical structures, in a more convenient viewing location for the user. The connection to the display may be achieved via a cable extending from the intubation device 140 or via a wireless communications connection which can avoid interference of user movements by a cable. In some examples, the display may be provided in the form of goggles worn by the user. It will be appreciated that this will conveniently allow the user to view the images presented from the video camera independently of the user's body and head position. The display may occupy the entire viewing area of the goggles or only a portion thereof, depending on the implementation.

In any of the above options for providing a display, the display may be surrounded by display light shielding (not shown), which may be configured so that the user can view the display whilst the display light shielding substantially prevents light emitted from the display from escaping beyond the display light shielding and the user's face. For example, in the above example of a display that is integrated with the intubation device 142, the display light shielding may be in the form of an extended hood surrounding the display, which engages with the user's face around the user's eye to substantially prevent the escape of light. In the case of a display provided in goggles worn by the user, the goggles may include light shielding surrounding in the form of a skirt of opaque, and preferably flexible material which can conform to the user's face around the user's eyes to substantially prevent the escape of light.

Figure 3A:
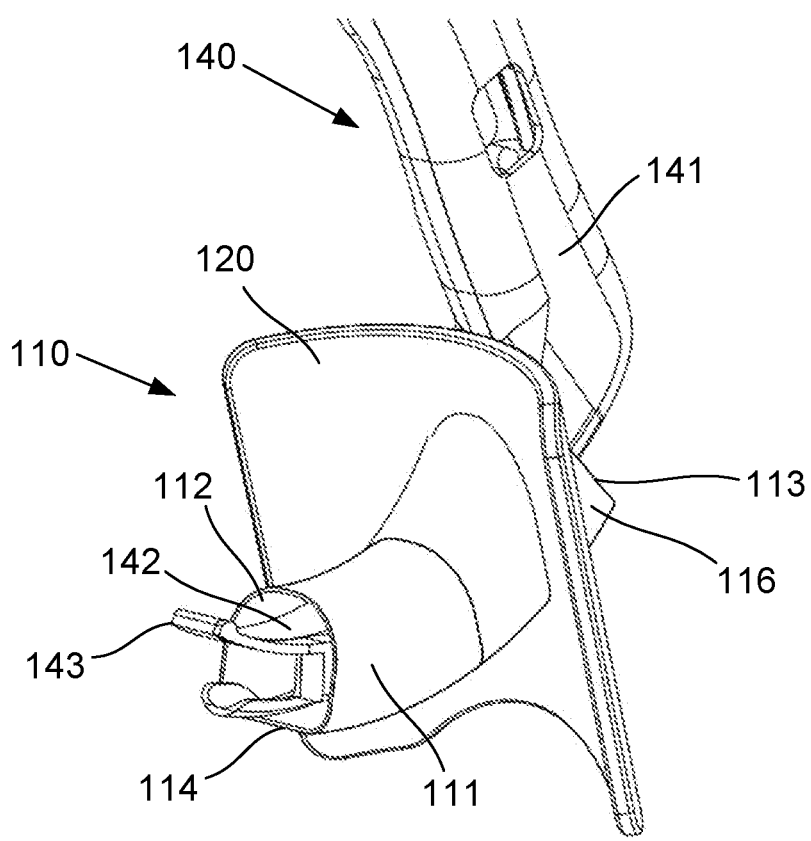
FIG. 3A is a perspective view of the shielded intubation guide of FIGS. 2A to 2D, with a blade portion of an intubation device inserted into the passageway of the shielded intubation guide.
Figure 3B:
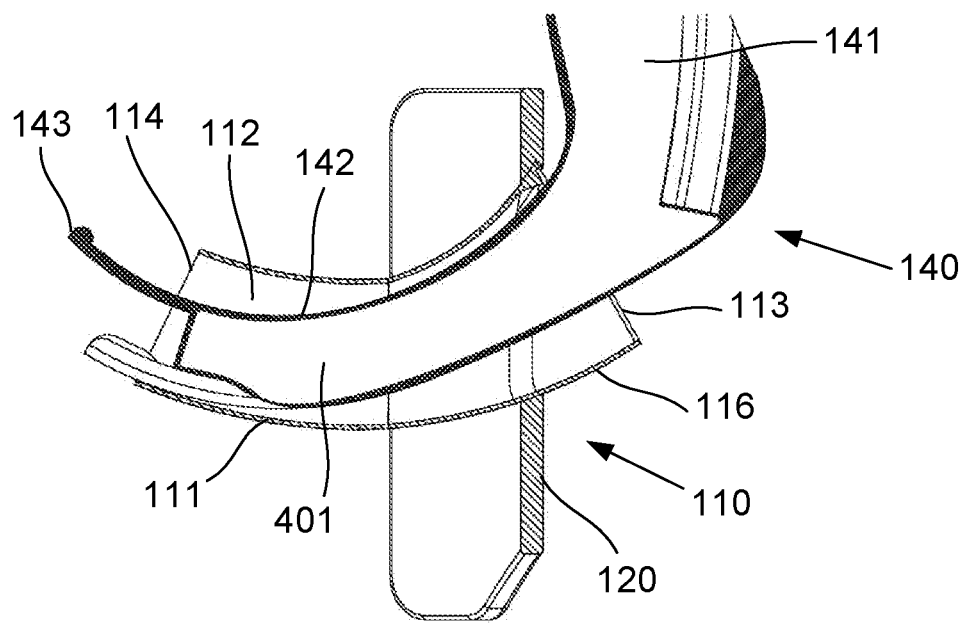
FIG. 3B is a cross section view of the shielded intubation guide and the inserted blade portion of the intubation device of FIG. 3A.

In any event, with regard to FIG. 1D, the endotracheal intubation is commenced by inserting the blade portion 142 of the intubation device 140 into the passageway 112 of the shielded intubation guide 110, through the proximal opening 113. The blade portion 142 of the intubation device 140 is passed through the passageway 112 of the shielded intubation guide 110 to position a distal tip 143 of the blade portion 142 proximate to the larynx 104 of the subject 100. Typically, the distal tip 143 will protrude through the distal opening 114, as can be seen in FIGS. 3A and 3B which provide detailed views of the positioning of the blade portion 142 of the intubation device 140 relative to the shielded intubation guide 110.

Light guided endotracheal intubation will typically be initiated during the insertion of the blade portion 142 of the intubation device 140 into the passageway 112 of the shielded intubation guide 110, by activating a light source of the intubation device 140.

The following discussion will describe the steps involved in performing a light guided endotracheal intubation procedure to facilitate further explanation of how the shielded intubation guide 110 may be used to provide a light shield and thereby substantially prevent light emitted from the light source from escaping from the mouth of the subject during the light guided endotracheal intubation procedure.

It should be appreciated that, whilst endotracheal intubation will typically be light guided, the escape of light from the mouth of the subject may not be considered a problem in many practical scenarios. In many cases, protection from fluids, droplets, and aerosols will be a greater concern. Therefore, it should be understood that embodiments of the shielded intubation guide 110 may only require light shielding functionality for particular scenarios, whilst it is expected that embodiments of the shielded intubation guide 110 will typically be used to reduce other emissions from the subject's mouth 102 such as fluids, droplets and aerosols in most practical scenarios.

Preferably, the light source will only be activated after the distal tip 143 of the blade portion 142 (and thus the light source which is typically located proximate thereto when provided on an intubation device 140) is initially inserted into the passageway 112, so that light is only emitted from the light source inside of the passageway 112, for guiding the insertion of the distal tip 143 through the passageway and into the desired positioning relative to the subject's anatomy.

The specific positioning of the distal tip 143 will depend of the particular configuration of the blade, but typically the distal tip 143 will be positioned around the epiglottis 107 and moved as required to expose the glottis of the subject. The distal tip 143 may engage with the vallecula inside the subject's trachea 105. As the blade portion 142 is moved, this may result in some movement of the shielded intubation guide 110 relative to the subject's mouth 102 and tongue 106.

FIG. 1E indicates, with dashed lines, regions inside the patient's airway that may be illuminated by the light source if it is activated during insertion of the blade portion 142, and particularly when the distal tip 143 is in position. Please note that different regions may be illuminated depending on the particular configuration of the intubation device 140, and specifically the location of the light source. In any event, the light source will usually be configured to illuminate the larynx 104 and surrounding anatomical structures such as the epiglottis 107, so that the user can move the distal tip 143 relative to these anatomical structures under the guidance of the light.

There will typically also be some illumination beyond these target areas, and this may include some light that is emitted back up the pharynx 103 and towards the mouth 102 as indicated in FIG. 1E. However, it will be appreciated that the shield 120 of the shielded intubation guide 110 can substantially prevent this light from escaping from the mouth 102 of the subject 100, by obstructing the light that is emitted towards the mouth 102. It will be appreciated that, if this light shielding functionality is desired, the shield 120 should be formed from an opaque material to therefore substantially prevent the transmission of light through the shield 120 itself.

As mentioned above, it is preferable that the shield 120 substantially covers the mouth 102 of the subject 100, and in examples where the shield 120 includes a flange extending outwardly from the body 111, it will be the flange that substantially covers the mouth 102 of the subject 100. It will be appreciated that, with an appropriately configured shield 120 that provides sufficient coverage of the mouth 102, the escape of light from the mouth can be effectively prevented during a light guided endotracheal intubation procedure.

It may be possible for some light to escape through the passageway 112, but it will be appreciated that any light emitted towards the passageway 112 will be significantly obstructed by the blade portion 142 inside the passageway 112. Moreover, as discussed in further detail below, the body 111 and the passageway 112 defined therewithin will often be curved, and this curvature of the body 111 may also help to prevent rays of light from being directly emitted along the passageway 112.

Figure 6:
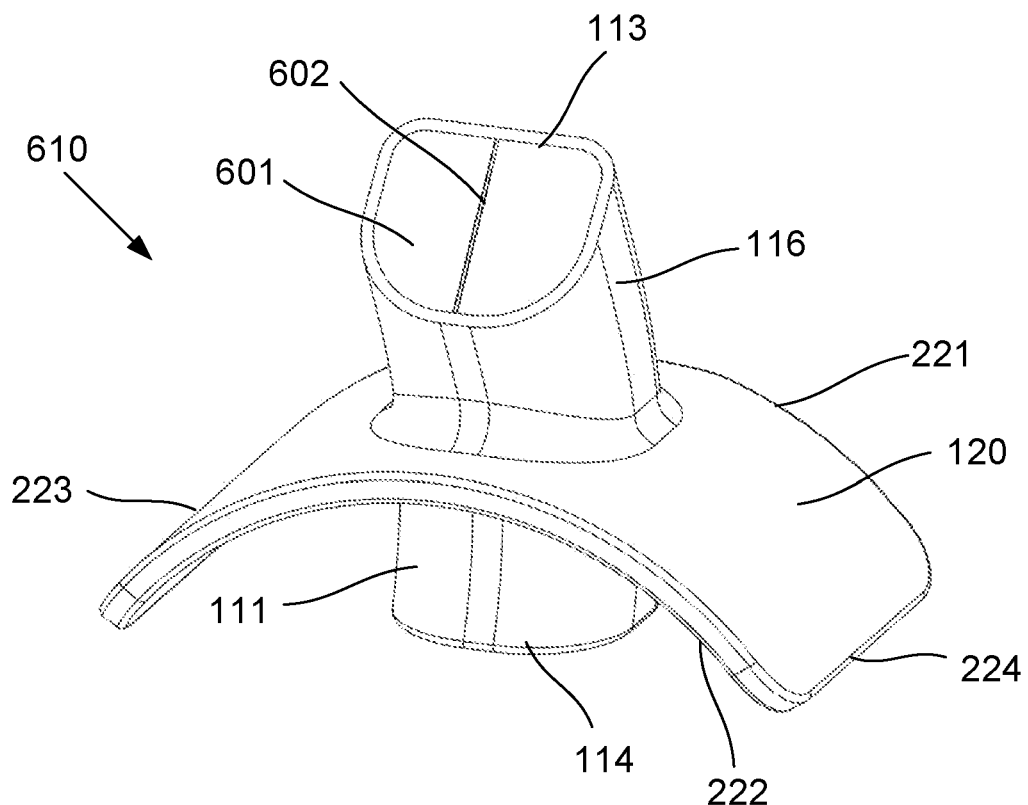
FIG. 6 is a perspective view of a third example of a shielded intubation guide having a membrane seal for sealing the proximal opening.

Furthermore, in some embodiments, the shielded intubation guide 110 may include a seal for covering the proximal opening 113, which can assist in preventing light from escaping through the passageway 112 and out of the proximal opening 113 while a light guided endotracheal intubation procedure is being performed. FIG. 6 shows an example of a shielded intubation guide 610 including a seal 601 covering the proximal opening 113. The seal 601 may be configured to normally be in a closed position for sealing the proximal opening and being moveable to an open position when the blade portion 142 of the intubation device 140 is inserted through the passageway 112. Thus, the blade portion 142 may be inserted through the seal 601 of the proximal opening 113 while the seal can help to block light emitted from a light source at the distal tip 143 of the blade portion 142.

It will be appreciated that a seal as described above can also be useful in reducing other emissions of fluids, droplets and/or aerosols from the subject's mouth or airway via the passageway 112 before and during the endotracheal procedure.

Now turning back to FIG. 1F, once the distal tip 143 has been moved to an appropriate position, the endotracheal tube 150 is advanced along the blade portion 142 of the intubation device 140 through the passageway 112 of the shielded intubation guide 110, to introduce the tip 151 of the endotracheal tube into the trachea 105 of the subject. It will be appreciated that the use of a single handed intubation device 140 allows the endotracheal tube 150 to be advanced by the user operating the thumb interface 144 using the thumb of the same hand holding the device. However, if a different form of intubation device that does not facilitate single handed intubation is used, the endotracheal tube 150 may be advanced manually, in a generally conventional manner.

In any event, the endotracheal intubation procedure including inserting the intubation device 140 and advancing the endotracheal tube 150 into the trachea 105 may be performed under the guidance of light emitted from the light source, while the shield 120 substantially prevents light from escaping from the mouth 102 of the subject 100. Accordingly, in this method, shielded intubation guide 110 may be used to allow light guided endotracheal intubation to be performed without the problem of escaping light.

For example, this method can enable a light guided endotracheal intubation procedure to be performed in dark conditions in combat scenarios, without light escaping from the subject's mouth and placing the military doctor or medic performing at risk of having their location revealed to the enemy and making them a target. It will be appreciated that this can expand the options available to military doctors or medics considering emergency intubations in combat scenarios, or the like.

However, as mentioned above, the shielded intubation guide 110 can be advantageously used to reduce emissions from the subject's mouth in all scenarios irrespective of whether or not this light shielding functionality is required, where this can assist, for example, in avoiding the transmission of infectious diseases from the subject to the user or other medical staff via droplet or aerosol emissions from the subject's mouth.

The endotracheal tube 150 will typically be a standard type of endotracheal tube and may include a balloon cuff (not shown), which can be inflated once the endotracheal tube 150 has been advanced into the desired position. It will be appreciated that the inflated balloon cuff can help to retain the endotracheal tube 150 in place in the subject's trachea 105.

Figure 1G:
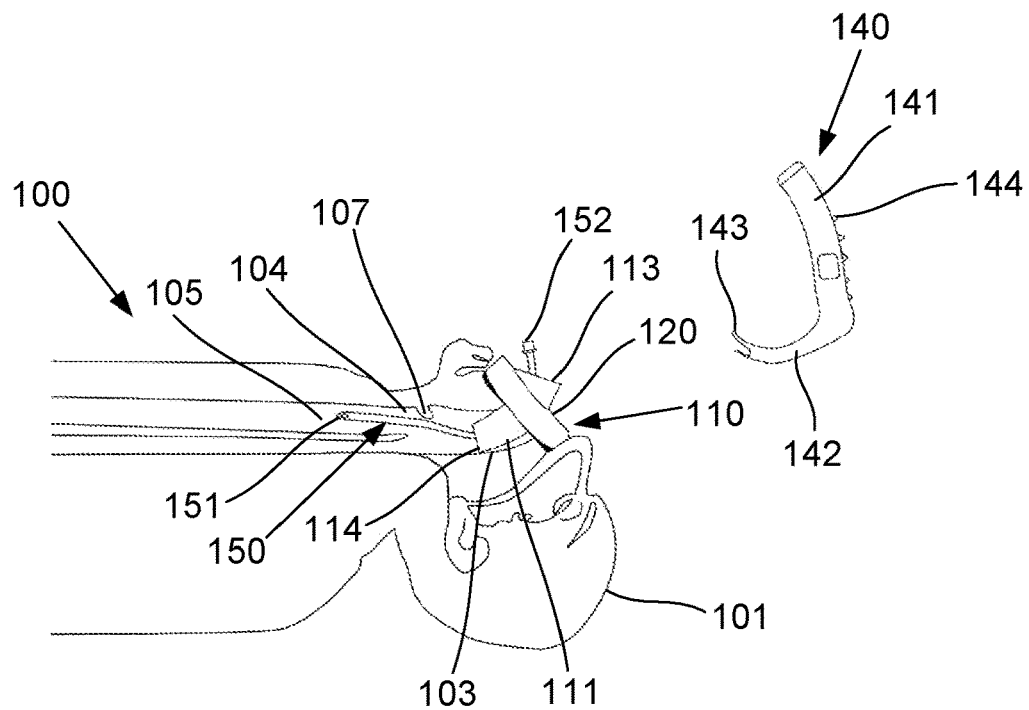

After the endotracheal tube 150 has been advanced into the trachea 105 of the subject 100 (and the balloon cuff inflated, if provided on the endotracheal tube 150), the light source may deactivated (if it was being used as part of a light guided endotracheal intubation procedure), and the intubation device 140 may be removed while leaving the endotracheal tube 150 in place in the trachea 105 as shown in FIG. 1G. This may be performed by withdrawing the blade portion 142 of the intubation device 140 from the shielded intubation guide 110, with the endotracheal tube 150 remaining in position as shown in FIG. 1G. At this stage, the shielded intubation guide 110 will still be left in place.

Then, the endotracheal tube 150 can be coupled to a ventilation source and used to provide ventilation to the subject 100. Typically, this will involve connecting the ventilation source (not shown) to a connector 152 at the proximal end of the endotracheal tube 150 so that ventilation will be provided via the endotracheal tube 150.

It should be appreciated that any suitable type of ventilation source may be used for ventilating the subject 100. For example, a manual bag-valve type ventilator may be used by connecting it to the connector 152 of the endotracheal tube 150 using a suitably configured ventilator connector. The ventilator connector will typically be a standard/universal connector type. The ventilator will generally be located outside the mouth of the subject. Alternatively, the ventilation source may be in the form of a powered mechanical ventilator, for example. In some embodiments, a more distant ventilator unit may be connected to the connector 152 of the endotracheal tube 150 by a length of flexible tubing, or the like.

Figure 1H:
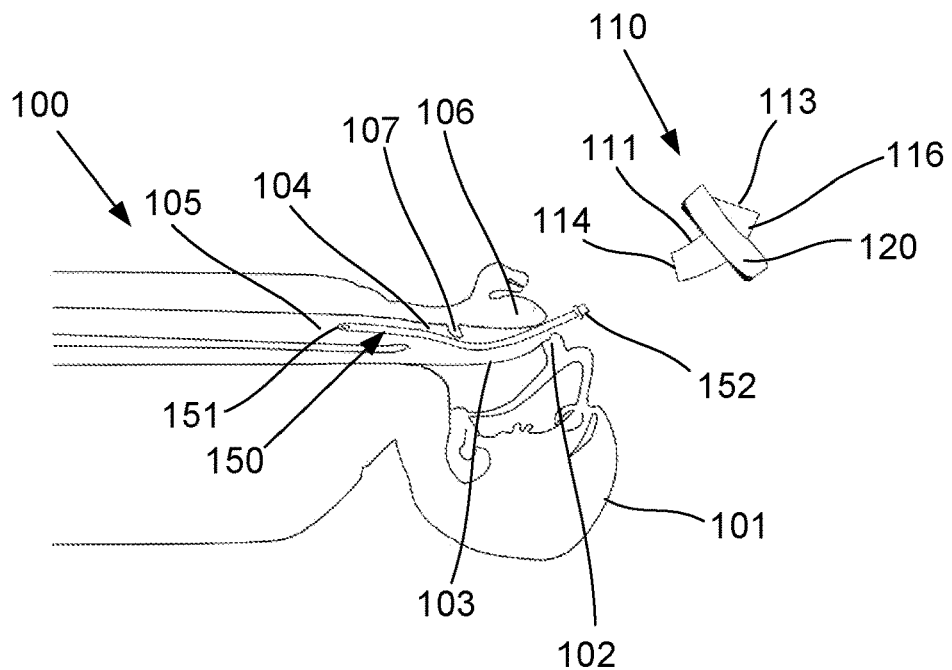

Once ventilation via the endotracheal tube 150 has been established, the shielded intubation guide 110 may be removed from the mouth 102 of the subject 100 as shown in FIG. 1H, leaving the endotracheal tube 150 in position for continued ventilation.

Figure 4A:
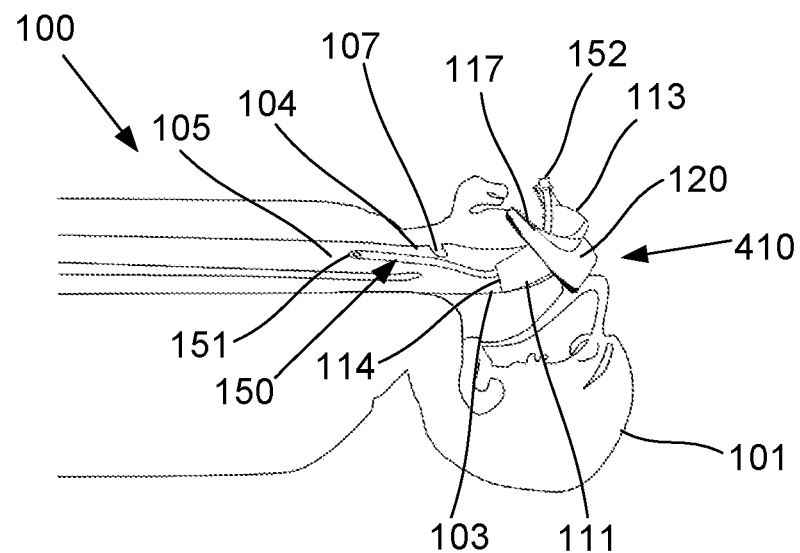
FIGS. 4A and 4B are cross section views showing steps of removing a second example of a shielded intubation guide after an endotracheal intubation procedure has been performed.
Figure 4B:
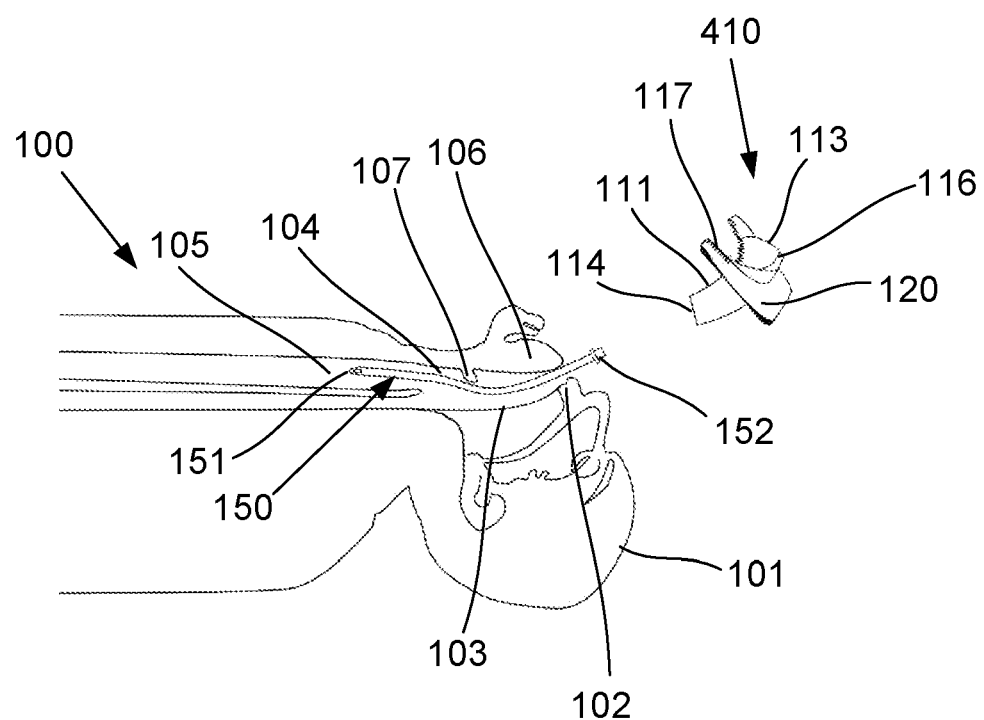

In some embodiments, the shielded intubation guide 110 may be configured to be broken along the passageway 112 and along a section of the shield 120 to allow its removal. Optional steps for breaking a second example of a shielded intubation guide 410 and removing it are illustrated in FIGS. 4A and 4B.

For instance, the example shielded intubation guide 410 may include a break line 117 in the body 111 and in a section of the shield 120, typically extending between the passageway 112 and an edge of the flange providing the shield 120. When using such a shielded intubation guide 410, the method may include breaking the shielded intubation guide 410, as per FIG. 4A, to allow the shielded intubation guide 110 to be removed while the endotracheal tube 150 remains in place, as shown in FIG. 4B.

Figure 5B:
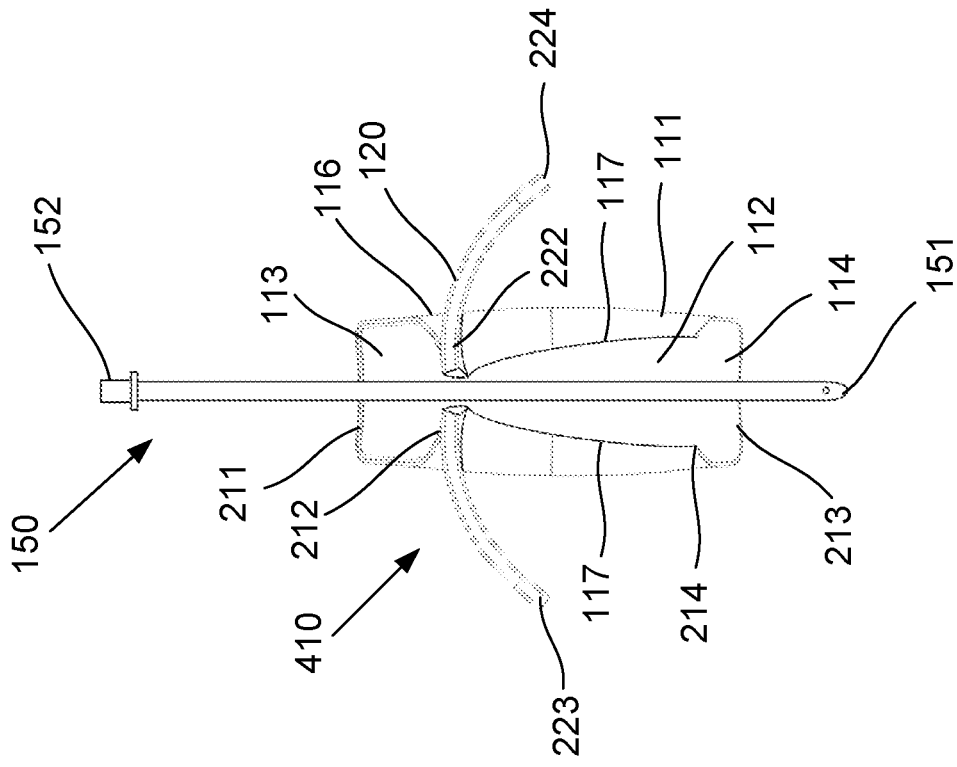
FIG. 5B is a bottom view of the shielded intubation guide and endotracheal tube of FIG. 5A, with the shielded intubation guide broken for removal of the endotracheal tube.
Figure 5A:
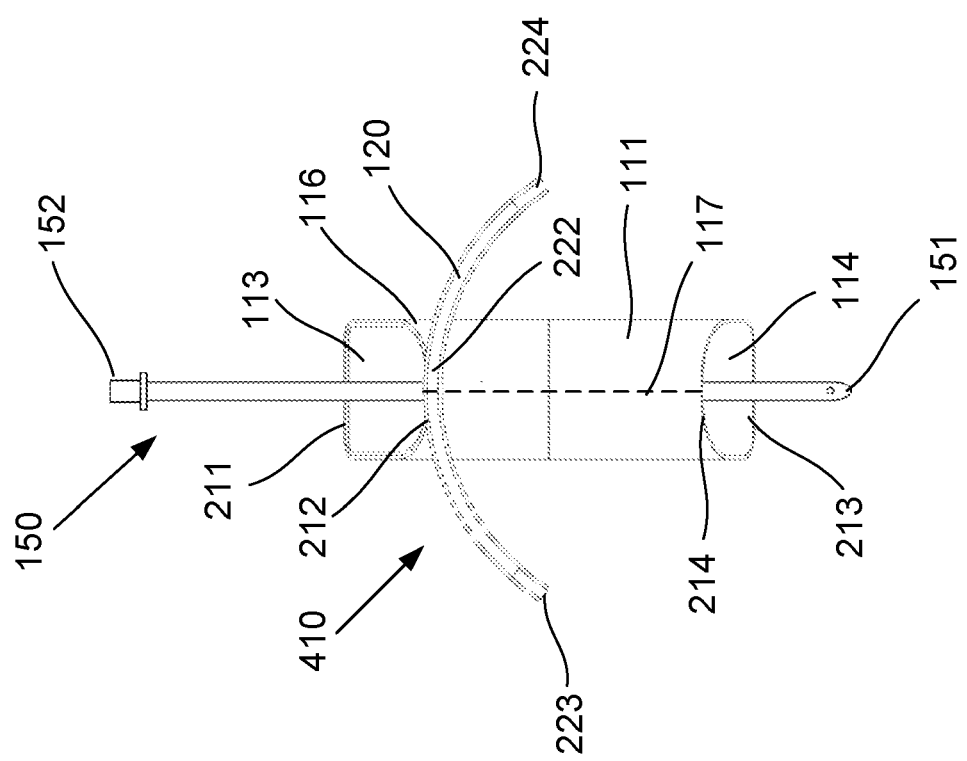
FIG. 5A is a bottom view of the second example of the shielded intubation guide of FIGS. 4A and 4B, with an endotracheal tube advanced through a passageway of the shielded intubation guide.

FIGS. 5A and 5B show detailed views of the shielded intubation guide 410 before and after being broken, with an endotracheal tube 150 extending through the passageway 112, to thereby illustrate how this will allow the shielded intubation guide 110 to be removed whilst leaving the endotracheal tube 150 in its deployed position.

It will be appreciated that this approach of breaking the shielded intubation guide 110 may avoid the need to pass the shielded intubation guide 110 over the connector 152 fitting at the proximal end of the intubation tube 150 and the need to disconnect the proximal end of the endotracheal tube 150 from the ventilator which would undesirably interrupt ventilation of the subject using the endotracheal tube 150. This can also avoid the risk of unintentionally displacing the endotracheal tube 150 from its delivered position and potentially losing the secure airway during removal of the shielded intubation guide 110.

In alternative examples, the shielded intubation guide 110 may include cutting marks (not shown) and be configured to be cut along the passageway 112 and along a section of the shield 120, by following the cutting marks. It will be appreciated that this will facilitate a similar functionality for facilitating removal of the shielded intubation guide 110 as discussed above, without the need to provide breakable portions in the construction of the shielded intubation guide 110, but with the added requirement for using a cutting tool.

The shielded intubation guide 110 may be designed so that the passageway 112 is fitted to the blade portion 142 of the intubation device 140 without having to build in an allowance for the tube fitting. This can help to reduce the escape of light emitted from the light source, around the blade portion 142 and through the passageway 112 during the light guided endotracheal intubation procedure. This can similarly help to reduce other emissions such as fluids, droplets and/or aerosols through the passageway 112 during any form of endotracheal intubation procedure, light guided or otherwise.

In some examples of the above described method, the shielded intubation guide 110 may be inserted into the mouth 102 of the subject 100 as shown in FIG. 1B, and, prior to endotracheal intubation being performed, the subject 100 may be ventilated using a ventilation mask and ventilator while the shielded intubation guide 110 is in position. Accordingly, it will be appreciated that the shielded intubation guide 110 will preferably be configured to allow this to occur, such as by being designed to fit under a standard ventilation mask.

It should be appreciated that any suitable type of ventilator may be used for ventilating the subject using the ventilation mask, as also discussed above for ventilation using the endotracheal tube. Typically, the ventilator will be in the form of a manual bag-valve mask ventilator connected to the ventilation mask, but the ventilator may alternatively be in the form of a powered mechanical ventilator, for example.

The process of ventilating the subject using the ventilation mask may include oxygenating the subject using the ventilation mask, such as by supplying oxygen gas from an oxygenation source to the ventilation port. In some cases, 100% oxygen may be supplied or air may be supplied at lower oxygen percentages. Nevertheless, it should be appreciated that oxygenation is not essential and the ventilation may be provided using atmospheric air without added oxygen. This may depend on whether a separate pressurised oxygen source is available, which may not be the case in some circumstances.

In any event, if ventilation is performed after insertion of the shielded intubation guide 110, this can continue until indefinitely until the user decides to proceed with the endotracheal intubation of the subject. For instance, the user may wish to continue ventilation until a desired blood oxygen saturation level is achieved, before intubating the subject. Alternatively, the shielded intubation guide 110 may be inserted by another user and the subject may be ventilated while waiting for an intubation specialist to become available for performing the endotracheal intubation of the subject.

It will be appreciated that the above method provides a new technique for allowing endotracheal intubation to be performed on a subject using the shielded intubation guide 110, wherein the shield 120 substantially reduces emissions from the mouth of the subject in use. In view of the above description of the method, it will be appreciated that the ability to perform the endotracheal intubation procedure will be enabled by the particular design of the shielded intubation guide 110, which will now be described in further detail with regard to FIGS. 2A to 2D.

As discussed above, the shielded intubation guide 110 includes an elongate body 111 defining a passageway 112 extending between a proximal opening 113 and a distal opening 114. The passageway 112 is configured for receiving a blade portion 142 of an intubation device 140. The shielded intubation guide 110 also includes a shield 120 at the distal opening 114. As mentioned above, the shield 120 is for substantially reducing emissions from the mouth of the subject in use.

As mentioned previously, the shielded intubation guide 110 is configured for insertion into a mouth 102 of the subject 100 so that the proximal opening 113 is positioned proximate to the mouth 102 of the subject and the distal opening is positioned proximate to a pharynx 103 of the subject, to thereby allow endotracheal intubation of the subject to be performed using an intubation device 140 and the shielded intubation guide 110.

As described above, the endotracheal intubation procedure will generally involve inserting the blade portion 142 of the intubation device 140 into the passageway 112 of the shielded intubation guide 110; positioning a distal end 143 of the blade portion 142 of the intubation device 140 proximate to the larynx 104 of the subject 100; and advancing an endotracheal tube 150 along the blade portion 142 of the intubation device 140 through the passageway 112 into a trachea 105 of the subject 100.

Further optional and/or preferred features of the shielded intubation guide 110 will now be discussed, with regard to FIGS. 2A to 2D.

As mentioned previously, the shield 120 is typically configured to substantially cover the mouth 102 of the subject 100 in use. In this example, the shield 120 includes a flange extending outwardly from the body as shown in FIGS. 2A to 2D, with the flange being configured to substantially cover the mouth 102 of the subject 100 in use. Typically, this flange surrounds the proximal opening 113.

In this example, the flange providing the shield 120 has a generally rectangular shape including superior and posterior edges 221, 222 and lateral edges 223, 224. In this case, the flange includes opposing lateral flange portions that are curved towards the distal opening 114. In other words, the lateral flange portions are curved in a way that will at least partially wrap around the face of the subject 100. This curved flange arrangement can assist in blocking any light that is emitted towards the subject's mouth 102 during a light guided endotracheal intubation procedure. This can also help to reduce other emissions from the subject's mouth 102 by minimising gaps between the flange providing the shield 120 and the face of the subject 100, through which fluids, droplets, aerosols or the like may be communicated.

In this embodiment, the flange providing the shield 120 includes a superior edge 221 having a recess 225 for aligning with a nose of the subject 100 in use. However, alternative embodiments of the shielded intubation guide 110 may include different configurations of the shield 120 whilst still providing the capability to substantially reduce emissions from the subject's mouth 102.

The flange may also be configured to provide an additional functionality of assisting in the correct insertion of the shielded intubation guide 110. In particular, the flange may help to prevent over-insertion of the shielded intubation guide 110 by abutting the subject's mouth 102, to thereby ensure that the proximal opening 113 remains positioned outside the mouth 102.

In some embodiments, the shielded intubation guide 110 may include straps or other suitable means for securing the shielded intubation guide 110 in position relative to the subject's mouth 102 after insertion. For example, the straps may be attached to lateral edges 223, 224 and either include loops for wrapping around the subject's ears, or may extend around the back of the subject's head. It will be appreciated that any means of securing the shielded intubation guide 110 to the subject may be used, in a similar manner to those used for securing oxygen masks or other devices worn on the subject's face.

The proximal opening 113 may be offset proximally from the flange and/or oriented at an angle relative to the flange. With regard to FIGS. 2A to 2D, it will be seen that the proximal opening 113 is provided at the end of a protruding portion 116 that protrudes proximally from the shield 120 such that the proximal opening 113 is located outside of the mouth 102. In this case, the proximal opening 113 is both offset from and oriented at an angle to the flange. In particular, a superior proximal opening edge 211 is offset further away from the flange compared to a posterior proximal opening edge 212.

In this case, the superior proximal opening edge 211 is substantially straight and leads into a substantially flat side of the body 111, which ends at a substantially straight superior distal opening edge 213. On the other hand, the posterior proximal opening edge 212 is curved and leads into a substantially flat side of the body 111, which ends at a curved posterior distal opening edge 214. It should be appreciated that the shapes of these edges and corresponding sides of the body 111 will generally be selected depending on the shape of the blade portion 142 of the intubation device 140, as discussed in further detail below.

As discussed above, in some examples the shielded intubation guide 110 may be configured to allow ventilation of the subject 100 using a ventilation mask and ventilator, after it is inserted and prior to guided endotracheal intubation being performed. To facilitate this, the shielded intubation guide 110 may be designed to fit under a standard ventilation mask, or to otherwise allow a ventilation mask to be used in conjunction with the inserted shielded intubation guide 110.

The elongate body 111 of the shielded intubation guide 110 may be curved as depicted in the example of FIGS. 2A to 2D. Such a curved configuration may be provided so that the shielded intubation guide 110 can better conform to the mouth 102 and airway anatomy of the subject 100 in use. Furthermore, as mentioned above, the curvature can also help to prevent light from being emitted through the passageway 112 around the blade portion 142 of the intubation device 140 during a light guided endotracheal intubation procedure. It is not essential that the shielded intubation guide 110 be curved, although it should be appreciated that whether it is curved or not, and the amount of curvature, will depend to at least some extent on the blade type of the intubation device 140.

The shielded intubation guide 110 may be formed from different materials having different levels of flexibility depending on requirements. For instance, embodiments of the shielded intubation guide 110 may be formed from a relatively flexible material such that the shielded intubation guide 110 may be allowed to at least partially deform in order to conform to the natural curvature of the mouth 102 and airway anatomy of the subject in use.

On the other hand, embodiments of the shielded intubation guide 110 may be formed from a relatively inflexible material, where a curvature of the body 111 will need to be selected to conform to the subject's anatomy without relying on substantial deformation of the intubation guide 110.

The use of a flexible material for forming the shield 120 may also be beneficial for allowing the shield 120 to conform to the face of the subject around the subject's mouth 102, although this is not essential and a more rigid material could be used.

The shielded intubation guide 110 will typically be formed from a suitable medical grade plastic material. In embodiments intended for providing light shielding functionalities as discussed above, at least the shield 120 should be formed from an opaque material to thereby ensure that light will not be transmitted through the light shield 120 and escape from the mouth 102 of the subject 100 during light guided endotracheal intubation procedures. In preferred embodiments, the entire shielded intubation guide 110 may be formed from the same opaque material. On the other hand, it should be understood that if light shielding functionality is not required, it will not be necessary to use an opaque material to form the shield 120 or other parts of the intubation guide 110, and in fact it may be desirable to make these parts transparent to facilitate visualisation of the oral cavity and the pharynx of the subject during the endotracheal intubation procedure.

It will be appreciated that the shielded intubation guide 110 may serve to allow the blade portion 142 of the intubation device 140 to be inserted into the airway of the subject 100 without interference with the subject's tongue and other anatomical structures which may otherwise obstruct the insertion of the blade portion 142 in use. This is especially advantageous since some embodiments of the shielded intubation guide 110 may prevent direct visualisation during insertion of the blade portion 142. However, it should be appreciated that other embodiments of the shielded intubation guide 110 may be configured to allow intubation under direct visualisation. In any event, it should be understood that the shielded intubation guide 110 will typically act to hold the tongue of the subject and typically to depress the tongue, i.e. to urge the tongue downwardly. This may depend on the particular shape and configuration of the shielded intubation guide 110, including the curvature and flexibility as discussed above.

The proximal opening 113 of the shielded intubation guide 110 is configured to allow the blade portion 142 to be inserted into the passageway 112 of the intubation guide 110 through the proximal opening 113. Preferably, the shielded intubation guide 110 will be designed to suit the intubation device 140 and particularly its blade portion 142. The intubation device 140 and endotracheal tube 150 that are used in the procedure may not necessarily be provided with any specific adaptations for use in a ventilated endotracheal intubation procedure as described above. Accordingly, the shielded intubation guide 110 may be provided separately to the intubation device 140 and endotracheal tube 150, provided the correct type of intubation device 140 and respective blade portion 142 are selected for the shielded intubation guide 110.

As mentioned above, some embodiments of the shielded intubation guide may include a seal, such as the example shown in FIG. 6. In that example, the shielded intubation guide 610 includes a seal 601 covering the proximal opening 113. The seal 601 may normally be in a closed position for sealing the proximal opening 113 and may be moveable to an open position when the blade portion 142 of the intubation device 140 is inserted through the passageway 112. The seal 601 may assist in reducing emissions from the subject's mouth or airway through the passageway 112.

Turning back to FIG. 1D, it will be appreciated that, when the blade portion 142 of the intubation device 140 is first inserted into the proximal opening 113, this may cause the seal 601 in the proximal opening 113 to move from the closed position to the open position, to thereby permit the blade portion 142 to pass through the proximal opening 113.

In preferred embodiments, the seal 601 will be biased towards the closed position, such that the seal 601 returns towards the closed position when the blade portion 142 of the intubation device 140 is removed from the passageway 112 after the procedure. The seal 601 may be configured to form a partial seal surrounding at least one of the blade portion 142 of the intubation device 140 and the endotracheal tube 150, thereby reducing or preventing emissions that may otherwise pass around the blade portion 142 or endotracheal tube 150 in use.

As mentioned above, the seal 601 may be moveable from a normally closed position (as shown in FIG. 6) to an open position when the blade portion 142 of the intubation device 140 is inserted through the proximal opening 113. In some embodiments, the seal 601 may include at least one resilient membrane configured to deform in response to the blade portion 142 being urged against the seal 601, to thereby define an opening for receiving the blade portion 142.

In one example, the seal 601 may include two or more resilient membranes that are each supported around a respective part of a perimeter of the proximal opening 113 and that each include a respective unsupported edge 602. The respective unsupported edges 602 may at least partially overlap in the closed position and separate to define the opening in the open position. Although overlapping edges 602 are preferred for more effective sealing, in some examples the edges 602 may be abutted in the closed position without any overlap.

In other examples, the seal 601 may include two or more resilient membranes that are supported around the perimeter of the proximal opening 113. The respective aperture of each resilient membrane may differ from the apertures of other resilient membranes in shape, location or orientation. In other words, the seal 601 may include multiple fully supported membranes with apertures such as slits that do not align or overlap, to thereby provide an enhance sealing effect.

In another example, the seal 601 may include a single resilient membrane that is supported around a perimeter of the proximal opening 113. The single resilient membrane may include an aperture that is substantially closed in the closed position and that stretches to define the opening in the open position. For instance, in some embodiments, the aperture may be a slit. In other embodiments, the aperture may be a pinhole, or may have any other geometry selected to allow a suitable opening to be formed for receiving the blade portion 142 of the intubation device 140. For instance, the aperture could be cross shaped or H shaped.

The at least one resilient membrane may be formed from any suitable membrane material, although typically a thin, flexible polymer material will be used. Preferably the membranes will be formed from an opaque material to ensure the escape of light is prevented, as discussed above for the shielded intubation guide 110.

It will be appreciated that, when the blade portion 142 is received in the proximal opening 113 (for example, as shown in FIGS. 3A and 3B), the seal 601 may be in the open configuration but may still provide effective sealing around the blade portion 142 to substantially prevent the escape of light around the blade portion 142 during the light guided intubation procedure, and/or to substantially reduce emissions of fluids, droplets, aerosols or the like around the blade portion 142 during any endotracheal intubation procedure. This will depend on the design of the seal 601 and also the design of the blade portion 142. For instance, if the seal 601 is configured to stretch around the blade portion 142 in the open position this may form a substantially airtight seal even when the blade portion 142 extends through the proximal opening 113.

It is also noted that the example of the shielded intubation guide 610 shown in FIG. 6 illustrates an alternative configuration of the body 111 and shield 120 compared to earlier examples. In this case, the proximal opening 113 is provided at the end of a longer protruding portion 116. The shield 120 includes longer lateral flange portions with lateral edges 223, 224 that will effectively wrap further around the subject's face, whereas the superior and posterior edges 221, 222 are located closer to the body 111. The portion of the body 111 that is inserted into the subject's mouth 102 is also shorter than in previous examples. It should therefore be understood that suitable embodiments of the shielded intubation guide 610 may include significant variations to the configuration of the body 111 and shield 120, whilst nevertheless providing similar functionalities as described above.

It will be appreciated that embodiments of the shielded intubation guide 110 may be allowed to move relative to the subject's anatomy as the blade portion 142 of the intubation device 140 is inserted through the passageway 112, and specifically as the distal tip 143 is moved to a suitable position to allow the endotracheal tube 150 to be advanced through the larynx 104 into the trachea 105 of the subject.

Figure 2A:
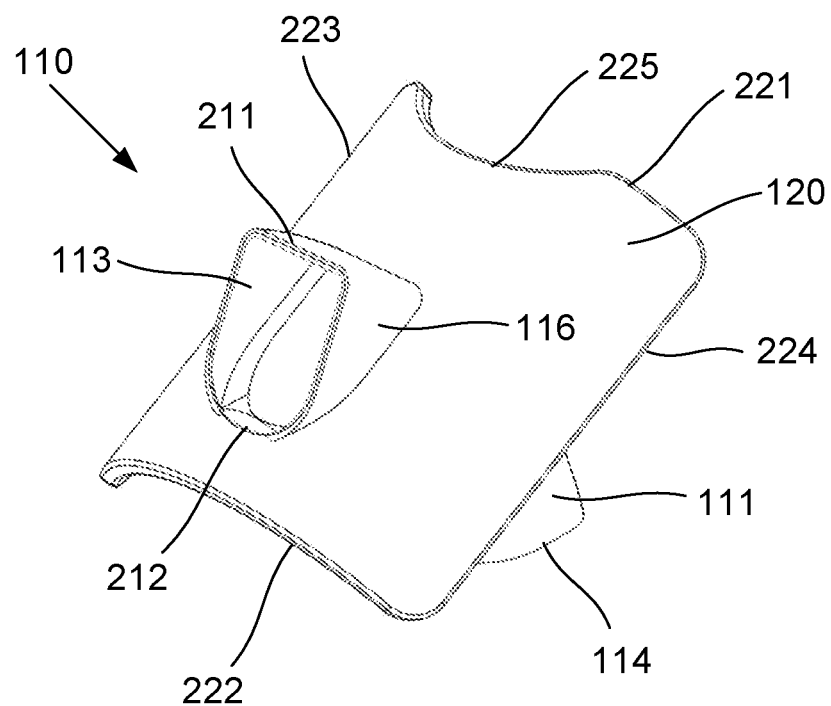
FIGS. 2A and 2B are perspective views of the first example of the shielded intubation guide of FIGS. 1A to 1H.
Figure 2B:
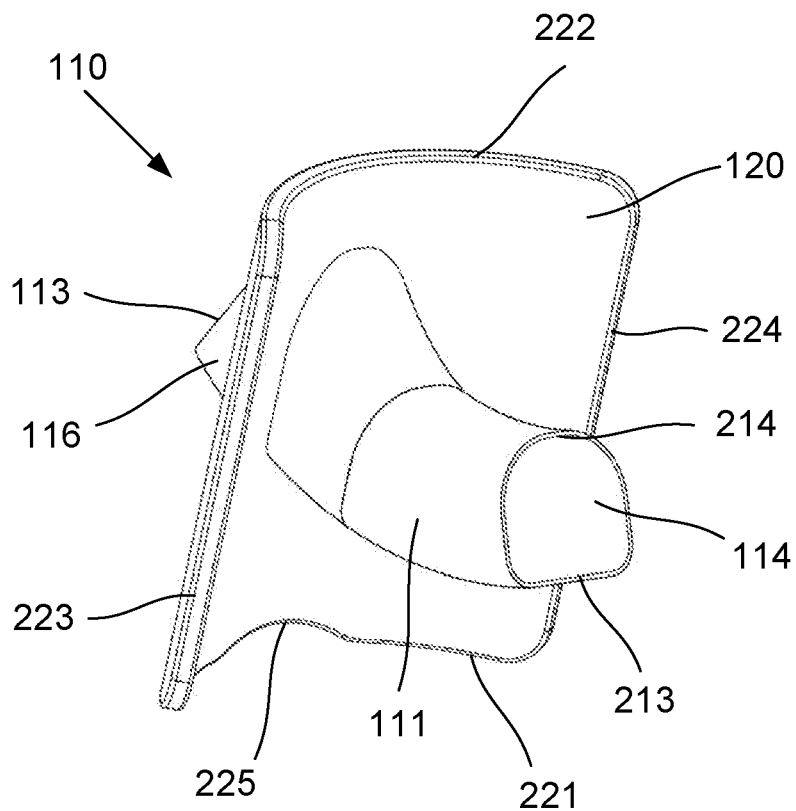
Figure 2C:
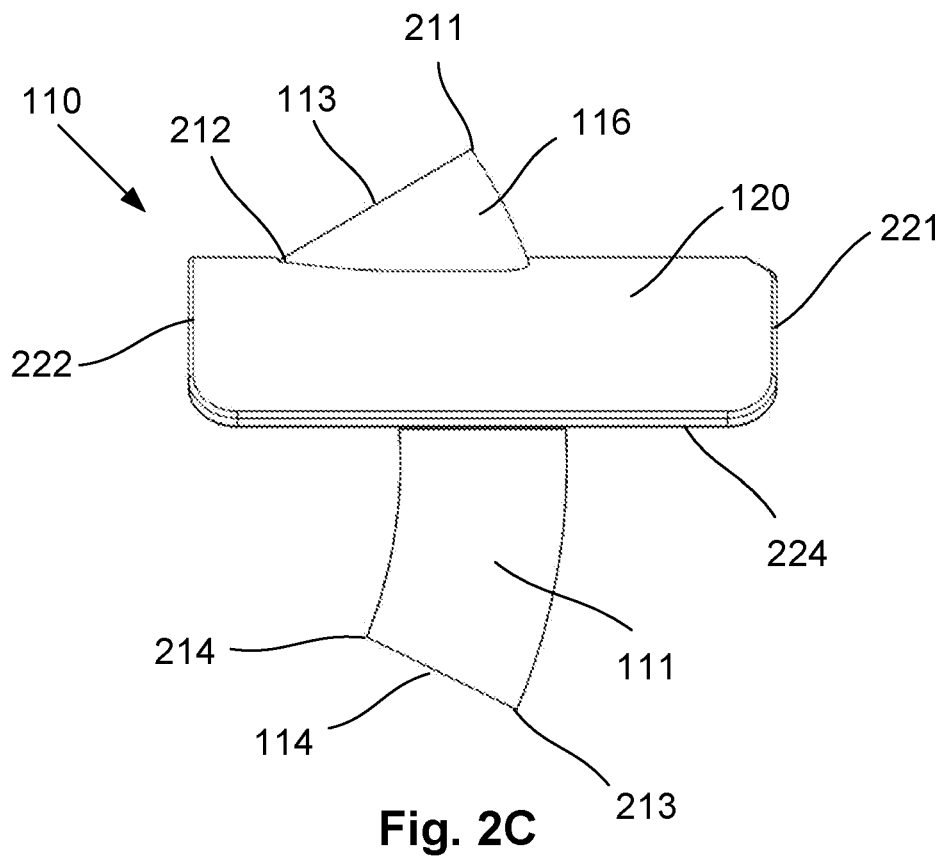
FIG. 2C is a side view of the shielded intubation guide of FIGS. 2A and 2B.
Figure 2D:
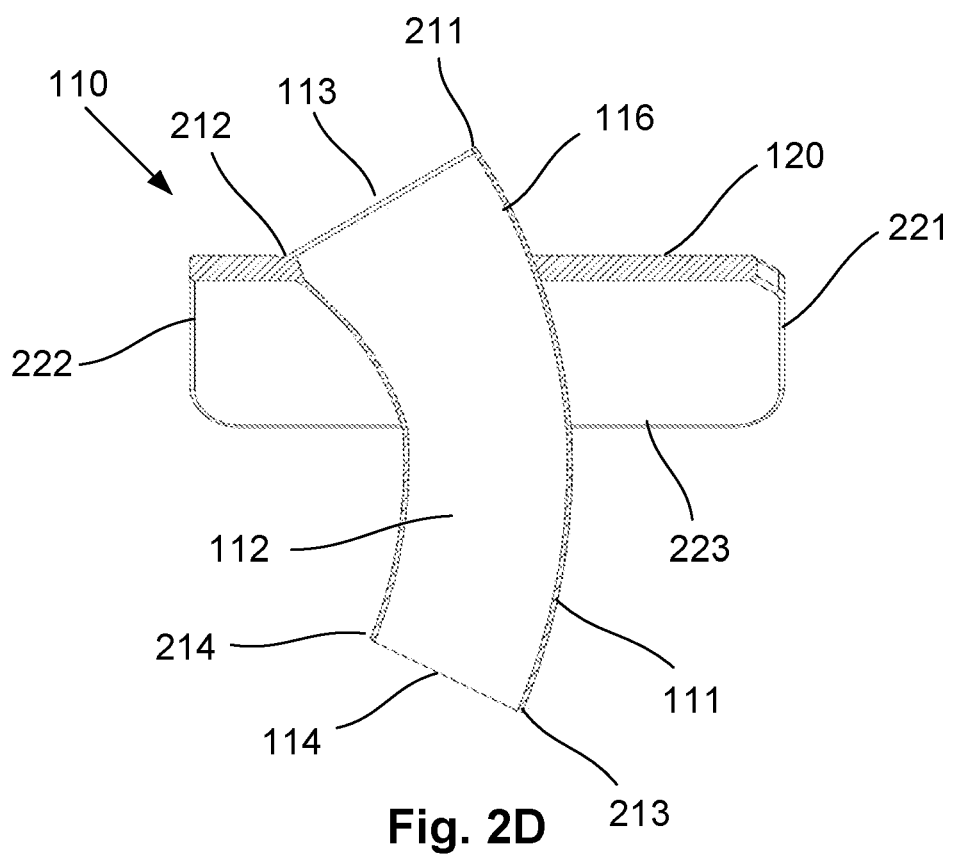
FIG. 2D is a cross section view of the shielded intubation guide of FIGS. 2A to 2C.

Turning back to the detailed example of the shielded intubation guide 110 shown in FIGS. 2C and 2D, it can be seen that the elongate body 111 may be defined as a thin walled body to define the passageway 112. The body 111 and the light shield 120 may be formed from a rigid, semi-rigid or flexible material such as a suitable medical grade plastic material. As mentioned above, if light shielding is required, it is desirable to form at least the light shield 120, and preferably the entire shielded intubation guide 110, using opaque material.

As mentioned above, it may be desirable to provide a shielded intubation guide 110 that is configured to be broken along the passageway 112 and along a section of the light shield 120, to facilitate removal of the shielded intubation guide 110 while the endotracheal tube 150 remains in place.

In the example of the shielded intubation guide 410 shown in FIGS. 4A and 4B and FIGS. 5A and 5B, the body 111 of the shielded intubation guide 410 includes a break line 117 extending longitudinally along a side of the passageway 112 and a section of the shield 120, to thereby allow the shielded intubation guide 410 to be broken along the break line 117. In this case, the break line 117 extends along the section of the shield 120 from the passageway 112 to the posterior edge 222 of the flange forming the shield 120.

The break line 117 could be formed by providing a region of significantly thinner material compared to the material making the walls of the body 111 and the shield 120, such that this thinner region would be breakable when opposing sides of the body 111 and light shield 120 are forcibly pulled apart. A hinge line may be defined on the opposite side of the passageway 112 so that the intubation guide 110 can be broken into two hingedly connected portions, to aid in removal while the endotracheal tube 150 remains in place.

In this case, it will be seen that the break line 117 is defined along a central plane of the shielded intubation guide 110. This break line 117 will be aligned with a sagittal plane of the subject 100 in use. However, it should be appreciated that the particular configuration of the break lines 117 in the depicted configuration is not essential, and the shielded intubation guide 110 may include a different arrangement to allow it to be broken to facilitate its removal.

The proximal opening 113 and the passageway 112 of the shielded intubation guide 110 will typically have cross sections that are selected to receive the blade portion 142 of the intubation device 140. It will thus be appreciated that the particular cross section shape will depend on the design of the intubation device 140. The proximal opening 113 and the passageway 112 will accommodate the cross section shape of the blade portion 142 as shown in FIG. 3B. However the shape may vary depending on the particular shape of the blade portion 142 at different points along its length.

Accordingly, a shape of the proximal opening 113 and the passageway 112 may be selected based on a cross section shape of the blade portion 142 of the intubation device 140. As mentioned above, the shielded intubation guide 110 may be curved, and if so, the curvature of the shielded intubation guide 110 may be selected based on a curvature of the blade portion 142 of the intubation device 140.

The degree of curvature may also depend on a range of other factors including the flexibility of the material used to form the body 111 and the airway anatomy of the subject. For instance, as discussed above, the use of a more flexible material may allow a straight or relatively uncurved body 111 to deform in use and conform to the blade portion 142 and/or the subject's airway. It should be appreciated that the curvature of the body 111 may be less critical if it is formed from a relatively flexible material. It should be noted, however, that there will be a practical limit to the flexibility of the shielded intubation guide 110 to prevent its collapse upon insertion into the subject's mouth.

Furthermore, the use of a relatively more flexible material to form the body 111 of the shielded intubation guide 110 may allow different sizes and shapes of the blade portion 142 to be accommodated, whereas the use of a relatively more rigid material may limit the range of blade types such that different shielded intubation guides 110 may need to be selected for different sizes and shapes of the blade portion 142.

It should be noted that a variety of different shapes and sizes of shielded intubation guides 110 may be provided to accommodate the range of different types, shapes and sizes of blades that may be used with the intubation device to suit patients having different ages, sizes and anatomical configurations. For instance, different shielded intubation guides 110 may be provided for use with pediatric, adult or obese subjects, and will be selected to correspond with the selected blade for the particular subject.

However, some of the above described techniques, such as the use of flexible materials to form the shielded intubation guide 110 may allow the same shielded intubation guide 110 to be used with a range of different blades.

The size of the proximal opening 113 and the passageway 112 may be selected based on the cross section size of the blade portion 142 of the intubation device 140. In some examples, the proximal opening 113 of the shielded intubation guide 110 may be deliberately constructed so that its size is smaller than a corresponding cross section size of the blade portion 142 of the intubation device 140. Similarly, the passageway 112 of the shielded intubation guide 110 may be deliberately constructed so that its size is smaller than a corresponding cross section size of the blade portion 142 of the intubation device 140. In this regard, it will be appreciated that the shielded intubation guide 110 may be configured to expand when receiving the blade portion 142. Forming the shielded intubation guide 110 from an expandable material can thus allow the blade portion 142 to be more tightly enclosed within the shielded intubation guide 110 in use.

A further example of a shielded intubation guide 710 is shown in FIGS. 7A to 7G. It will be appreciated that this shares many common features with the previous examples and the same reference numerals have been used to refer to common features. However, this example illustrates a number of optional construction features which will now be described.

In this example, the shielded intubation guide 710 may include a removable cap 730 for closing the proximal opening 113 when the blade portion 142 of the intubation device 140 is not being inserted into the passageway 112 of the shielded intubation guide 110.

Figure 7A:
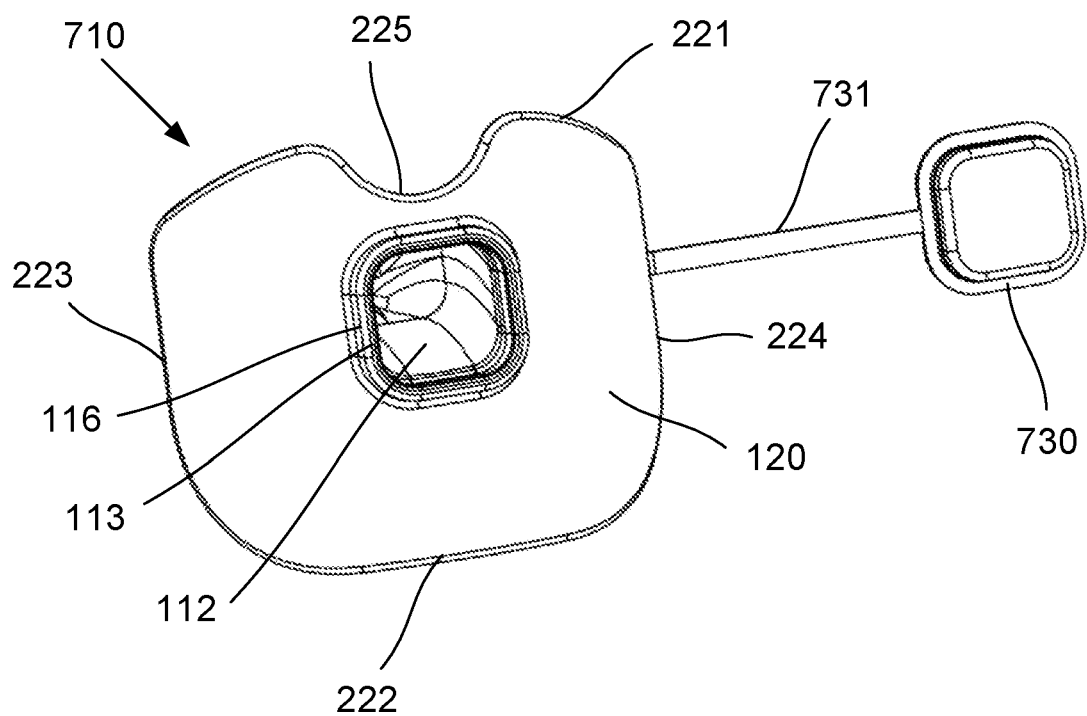
FIG. 7A is a perspective view of a fourth example of a shielded intubation guide having a removable cap, with the cap in an open position.
Figure 7B:
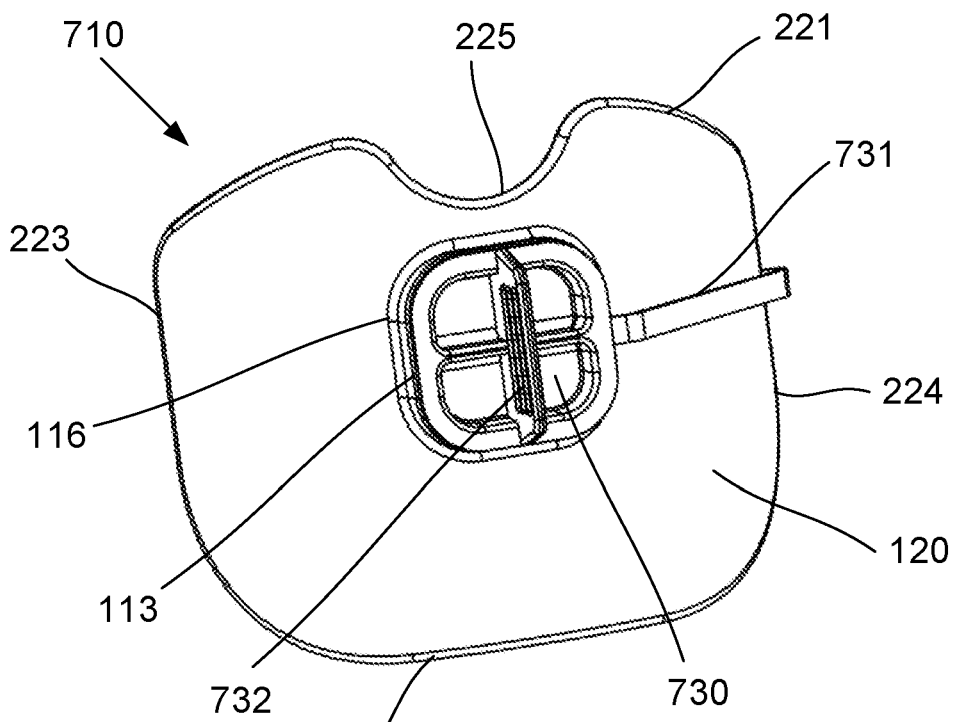
FIGS. 7B and 7C are perspective views of the shielded intubation guide of FIG. 7A, with the cap in a closed position.

In this case, the cap 730 is provided as an integral part of the shielded intubation guide 710 and is coupled to the shield 120 by a retaining member 731 extending from one of the lateral edges 224 of the shield 120. FIG. 7A shows the cap 730 removed from the proximal opening 113 thereby allowing insertion of the blade portion 142 of the intubation device 140 into the open passageway 112. On the other hand, FIG. 7B shows the cap 730 in a closed position for sealing the proximal opening 113. When the cap 730 is in the closed position, the cap 730 may fit inside the proximal opening 113 or engage with a rim surrounding the proximal opening 113. The cap 730 may include a tab 732 as seen in FIG. 7B, for allowing a user to remove the cap 730 by gripping and pulling the tab 732.

Figure 7C:
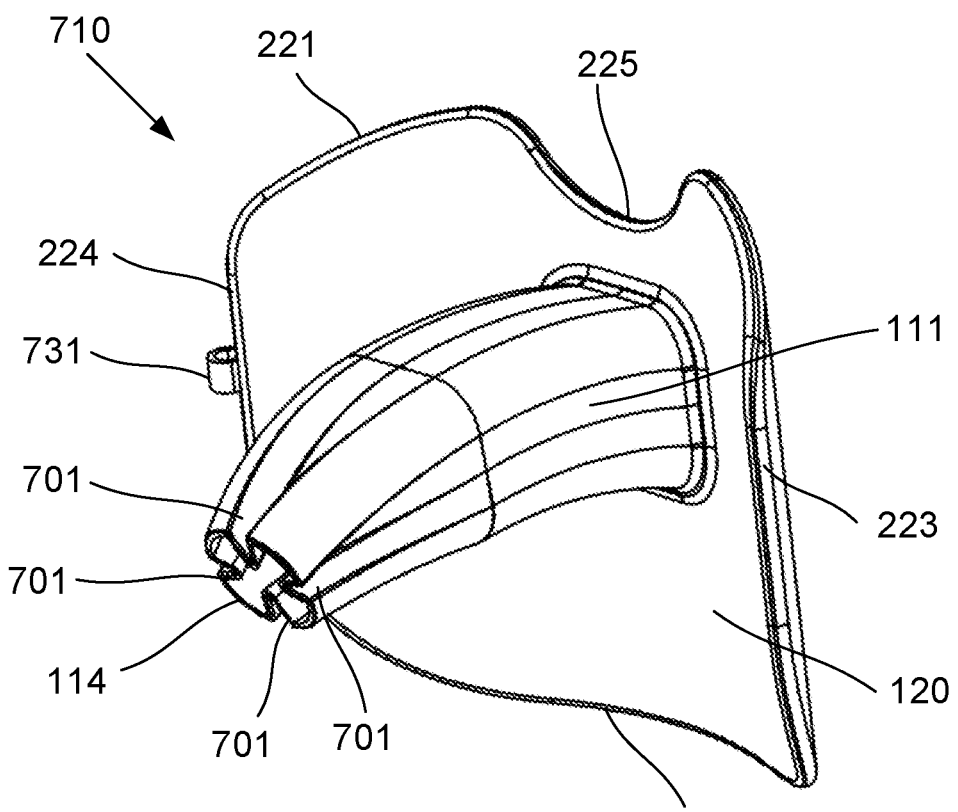
Figure 7D:
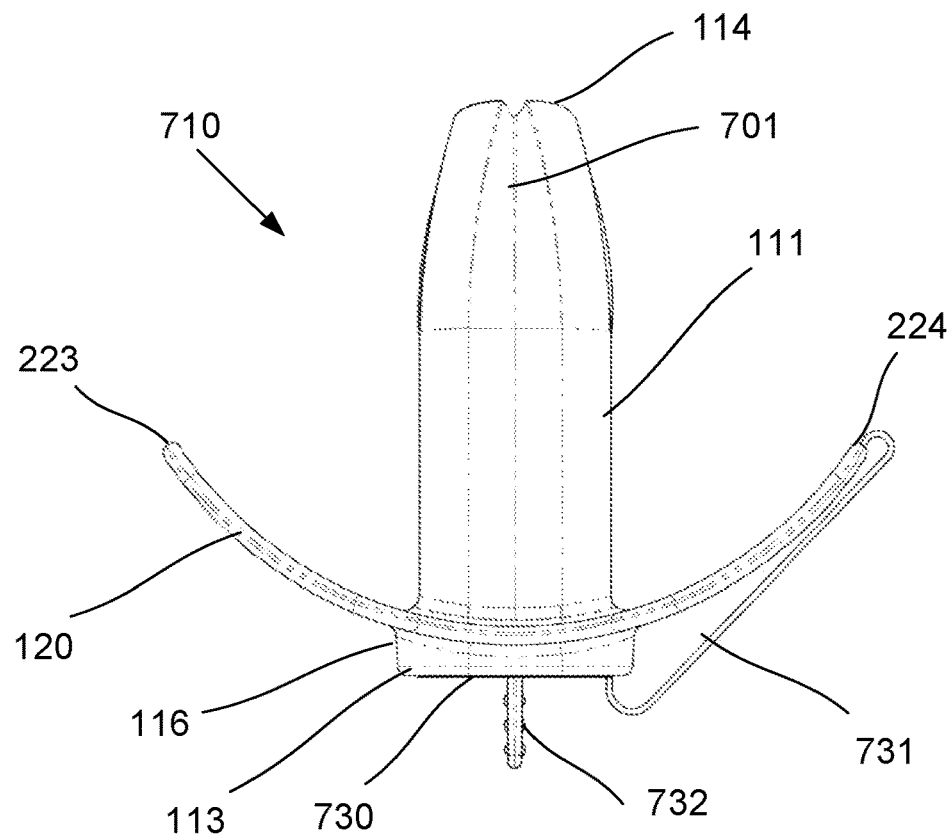
FIG. 7D is a top view of the shielded intubation guide of FIG. 7A, with the cap in the closed position.
Figure 7E:
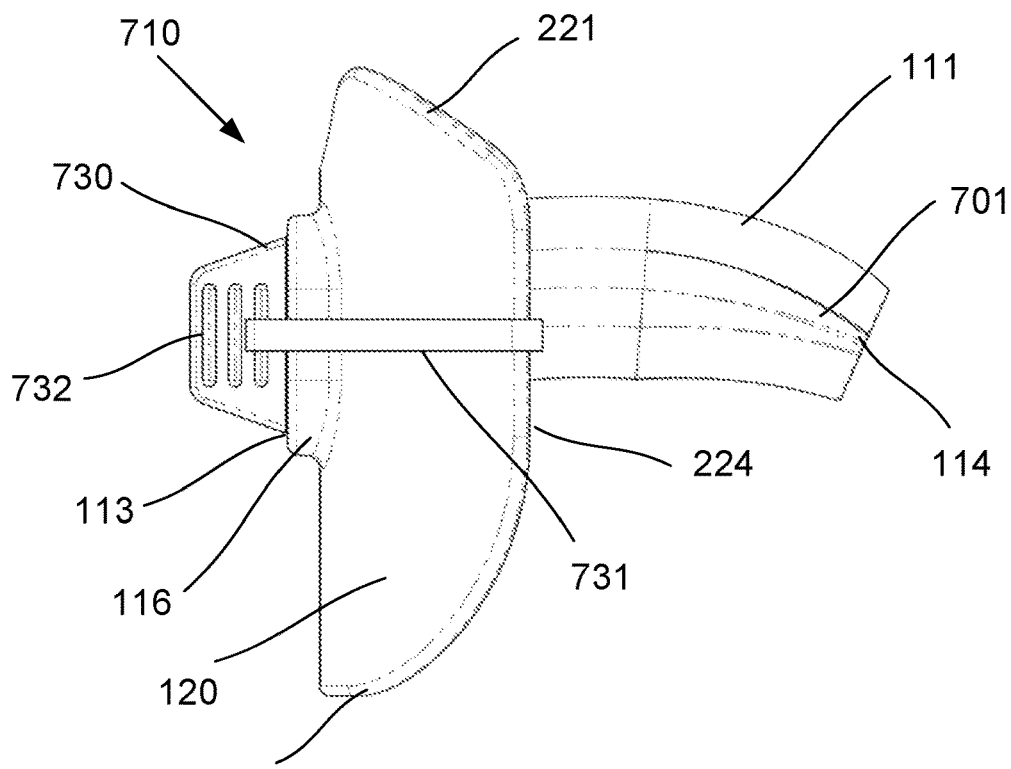
FIG. 7E is a side view of the shielded intubation guide of FIG. 7A, with the cap in the closed position.
Figure 7F:
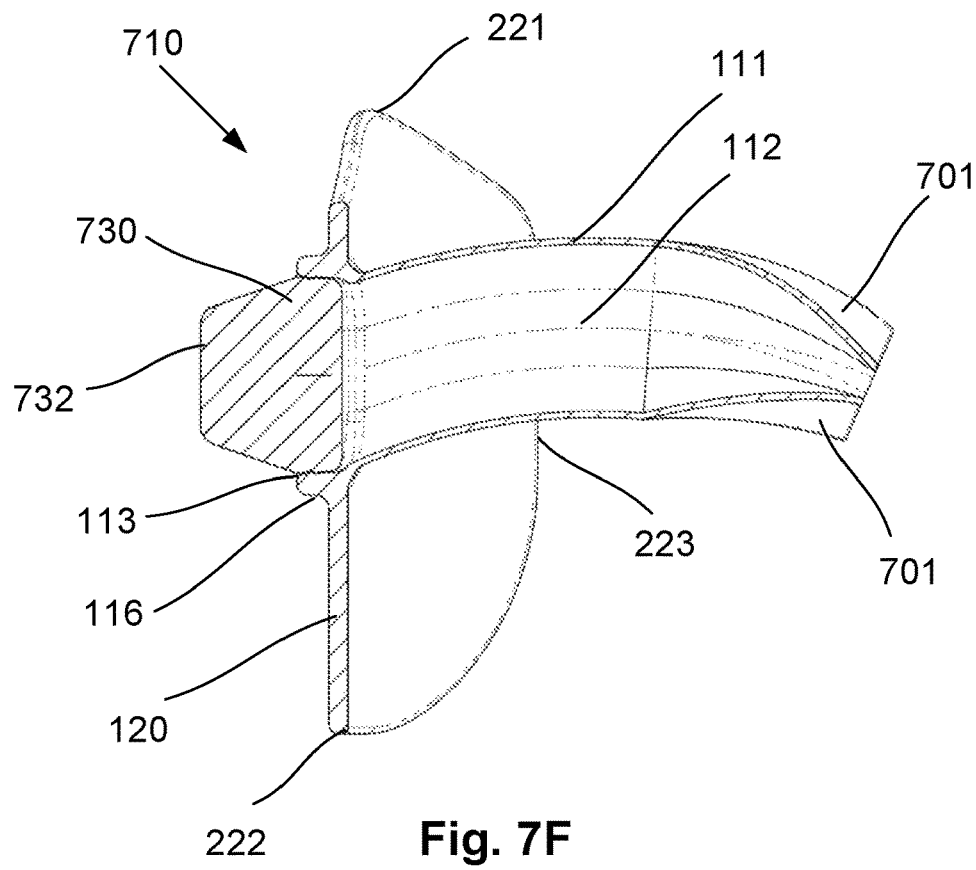
FIG. 7F is a cross section view of the shielded intubation guide of FIG. 7A, with the cap in the closed position.
Figure 7G:
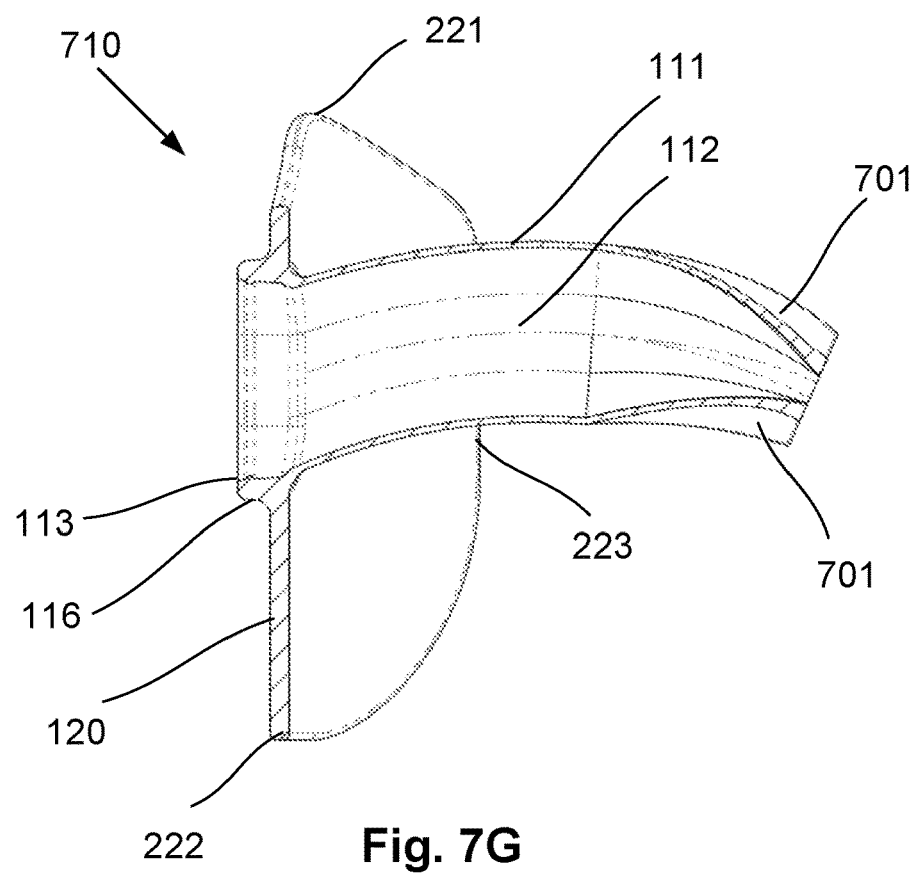
FIG. 7G is a cross section view of the shielded intubation guide of FIG. 7A, with the cap in the open position.

Further details of the cap 730 in the closed position can be seen in the cross section view of FIG. 7F, whilst the structure of the proximal opening 113 can be better observed in with the cap 730 removed as shown in the cross section view of FIG. 7G.

Typically the cap 730 will remain in place for sealing the proximal opening 113 during the insertion of the shielded intubation guide 110 into the mouth of the user, thereby substantially reducing emissions through proximal opening while the cap is in place. The cap 730 may then be removed prior to inserting the blade portion 142 of the intubation device 140 into the passageway 112 of the shielded intubation guide 110.

It will be noted that, in this example of the shielded intubation guide 110, the flange providing the shield 120 is laterally curved to follow the shape of the subject's face in use, as best seen in FIGS. 7D and 7E. With further regard to these Figures, it will be noted that this example of the shielded intubation guide 110 has a significantly reduced protruding portion 116 compared to previous examples.

Turning back to FIG. 7C, it will be seen that the body 111 of the shielded intubation guide 710 is curved as discussed in above examples. In this case, the walls of the body 111 include respective expandable regions 701 extending longitudinally from the distal opening 114 at least partially along the passageway 112. These expandable regions 701 allow the body 111 to expand circumferentially in use. These expandable regions 701 may be provided by forming flutes in the walls of the body 111 which are normally in a collapsed state as shown in FIG. 7C, but which are capable of expanding to accommodate the blade portion 142 of the intubation device 140 when it is inserted through the passageway 112 and the distal opening 114. Further details of these expandable regions can be seen in the cross section views of FIGS. 7F and 7G.

Figure 8:
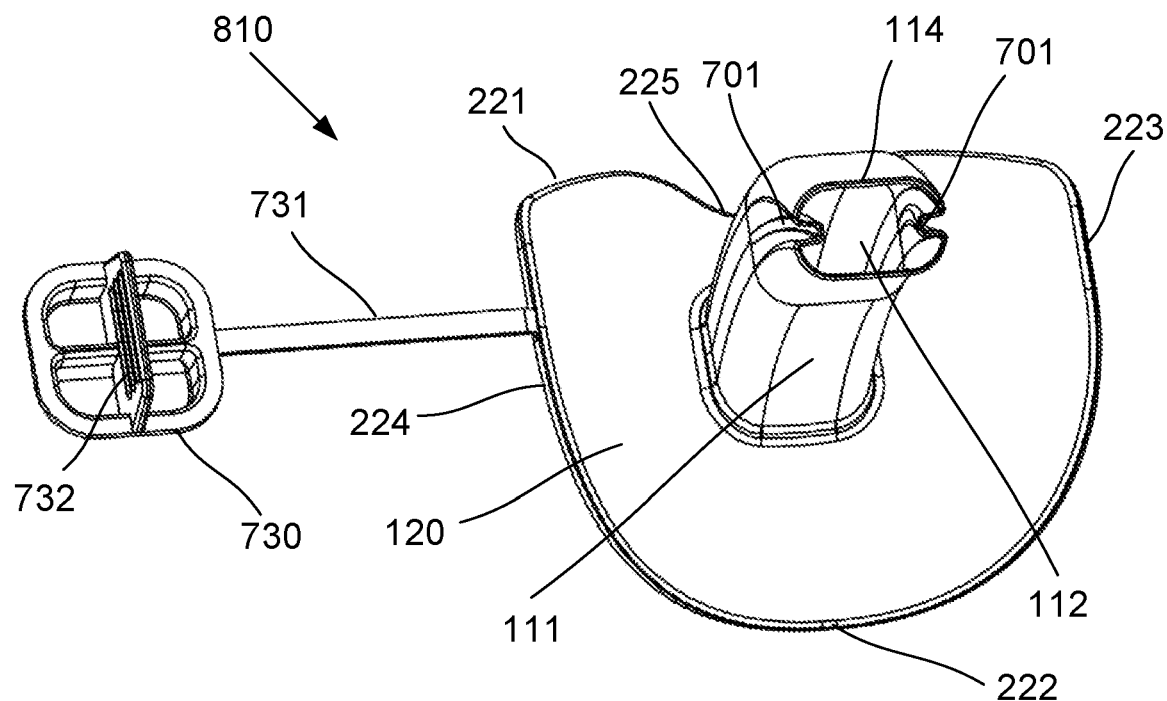
FIGS. 8 and 9 are perspective views of respective fifth and sixth examples of a shielded intubation guide, illustrating alternative configurations of expandable regions extending from the distal opening.
Figure 9:
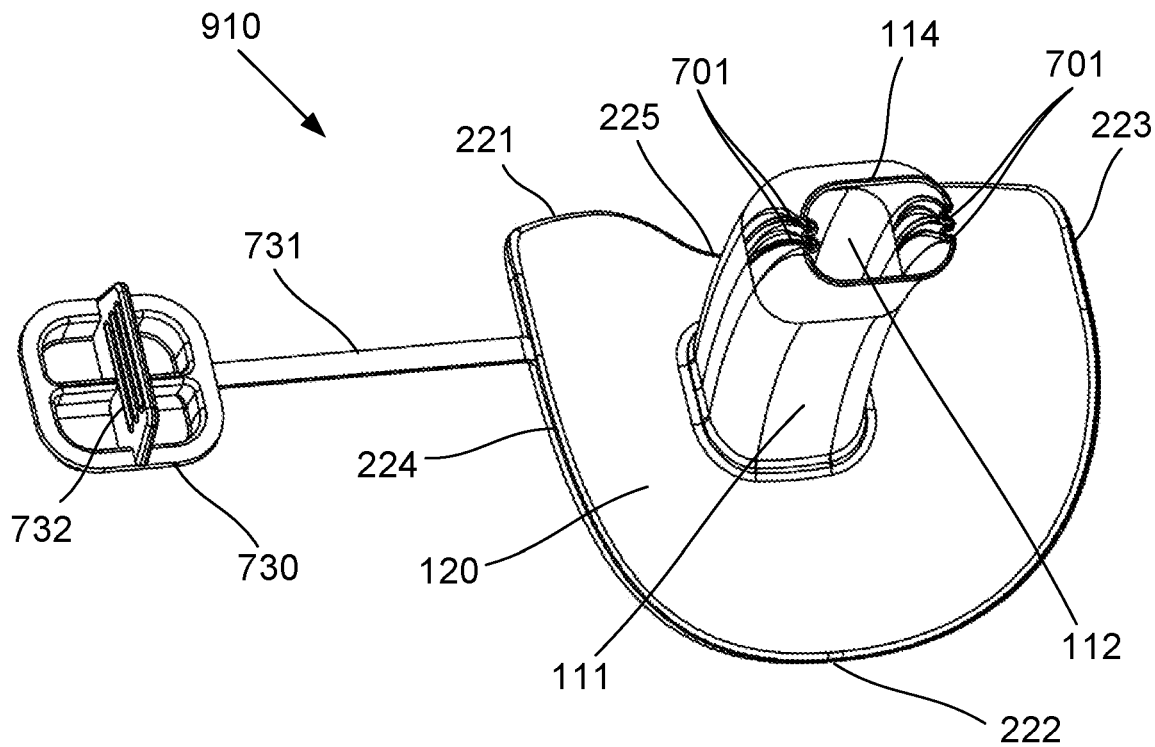

Two more examples of shielded intubation guides 810 and 910 are shown in FIGS. 8 and 9, respectively. These are essentially the same as the previously described shielded intubation guide 710, but provides different examples of possible configurations of the expandable regions 701 extending longitudinally from the distal opening 114 at least partially along the passageway 112.

In the first example as shown in FIG. 8, one expandable region 701 is provided in each of the lateral walls of the body 111, but in contrast to the previous example, there are no expandable regions 701 provided in the upper and lower walls of the body 111.

In the second example as shown in FIG. 9, two expandable regions 701 are provided in each of the lateral walls of the body 111. Providing more than one flute can provide enhanced expandability and ensure that the body 111 normally has a flatter profile which can facilitate insertion of the shielded intubation guide 910 whilst still allowing insertion of the blade portion 142 of the intubation device 140. This can help to reduce damage to the balloon cuff of the endotracheal tube during the procedure.

It is generally desirable to avoid pushing the tongue backwards during the endotracheal intubation procedure, so ideally the tongue position should be maintained without displacing it too far. In the example of the shielded intubation guide 910 in FIG. 9, the substantially flattened configuration of distal end of the body 111 resulting from the use of multiple expandable regions 701 can allow this part of the shielded intubation guide 910 to more easily traverse the tongue and palette without pushing the tongue backwards, and without touching the pharynx, so as to also avoid inducing a gag reflex in the subject.

It should be appreciated that, whilst the expandable regions 701 discussed above have been shown in the form of flutes in the walls of the body 111, this is only an example of a suitable construction technique for providing expandable regions for allowing the body to expand circumferentially, and numerous other techniques will be available to those skilled in the art. For instance, suitable expandable regions may be formed using a relatively more flexible material compared to the rest of the body 111, or by providing overlapping wall surfaces that can slide relative to one another to facilitate expansion of the body 111, circumferentially.

Figure 10:
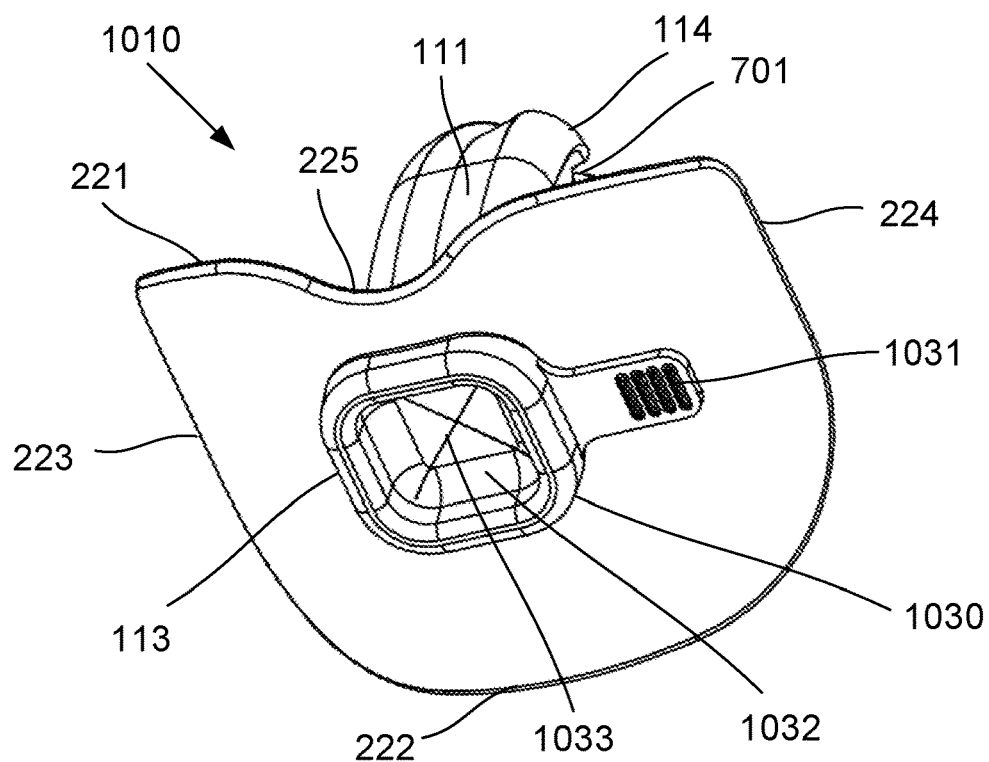
FIG. 10 is a perspective view of a seventh example of a shielded intubation guide and a separate removable cap-seal part.

Another example of a shielded intubation guide 1010 is shown in FIG. 10. In this case, a separate removable cap-seal part 1030 is provided in place of the integral cap 730 shown previously. The cap-seal part 1030 in this example also has a slightly different design compared to the previous integral cap 730, particularly in that the cap-seal part 1030 engages with the protruding portion 116 in which the proximal opening 113 is defined, and has a removal tab 1031 extending to a side of the cap-seal part 1030 to allow removal with a peeling action as opposed to a pulling action.

Furthermore, in this example, the cap-seal 1030 includes an integral seal 1032 for covering the proximal opening 113, the seal 1032 normally being in a closed position for sealing the proximal opening 113 and being moveable to an open position when the blade portion 142 of the intubation device 140 is inserted through the proximal opening 113, thereby functioning in a similar fashion to the seal 601 of the earlier described embodiment of the shielded intubation guide 600 in FIG. 6. The cap-seal 1030 may include a seal membrane 1032 having and one or more slits 1033 or other orifices formed in it to thereby permit the blade portion 142 upon insertion.

As per the seal 601 described above, the cap-seal 1030 is intended to allow improved protection from fluids, aerosols or droplets even while a laryngoscope blade and endotracheal tube are positioned inside the proximal opening 113, by partially sealing the proximal opening 113 around any inserted object. If the laryngoscope blade and endotracheal tube are removed, the seal membrane 1032 will return to its original closed position to thereby reform a full seal.

It should be appreciated that, by providing the seal 1032 in the separate cap-seal part 1030, this allows the cap-seal part 1030 to be formed from a suitable resilient material, such as a silicone or rubber material, whereas the shielded intubation guide 1010 can be formed entirely from a different material. This can greatly simplify manufacture of the shielded intubation guide 1010.

It should also be appreciated that the use of a removable cap may be especially desirable for use with a non-video or direct vision laryngoscope, to thereby allow the user to have an unobstructed visual line of sight into the proximal opening 113 and through the passageway 112.

Figure 11A:
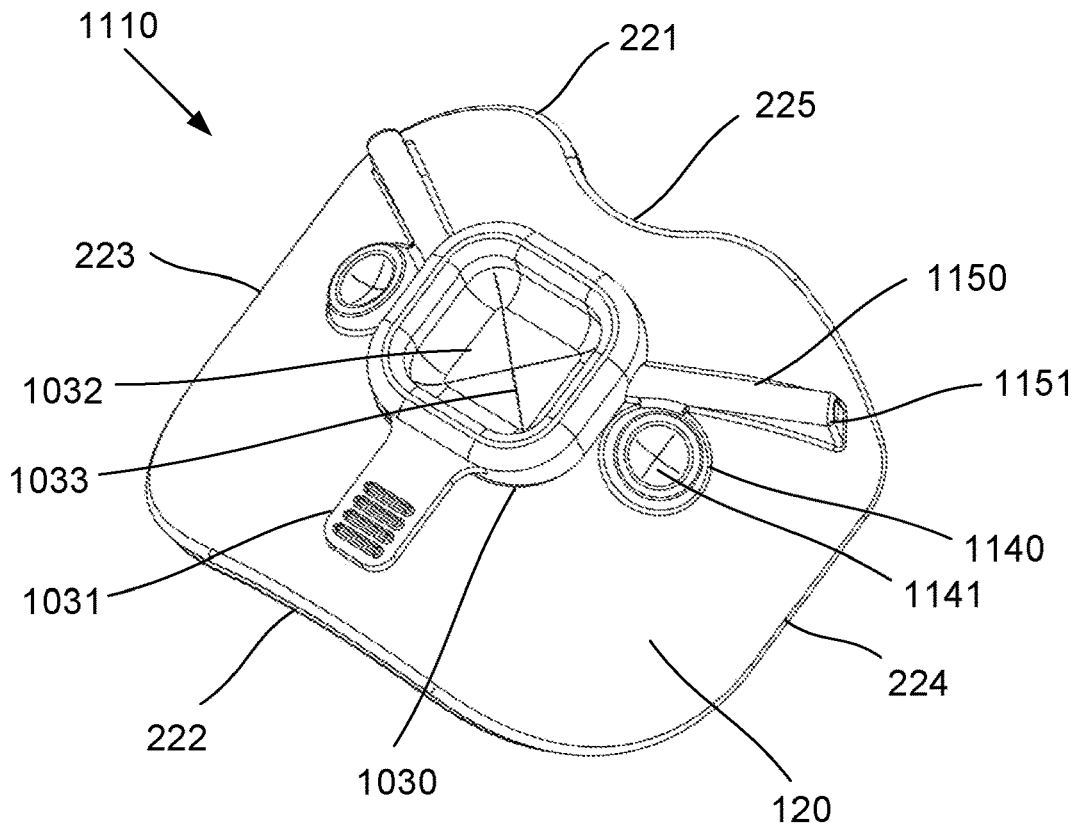
FIGS. 11A to 11C are perspective views of an eighth example of a shielded intubation guide.
Figure 11B:
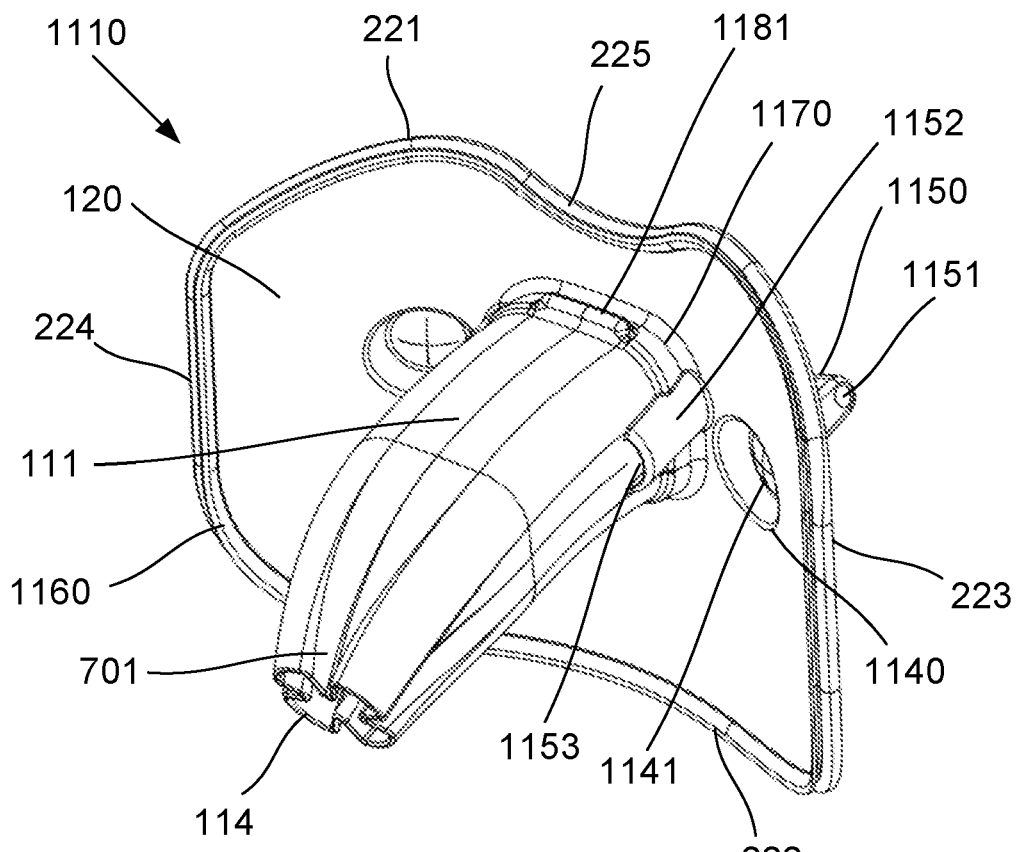
Figure 11C:
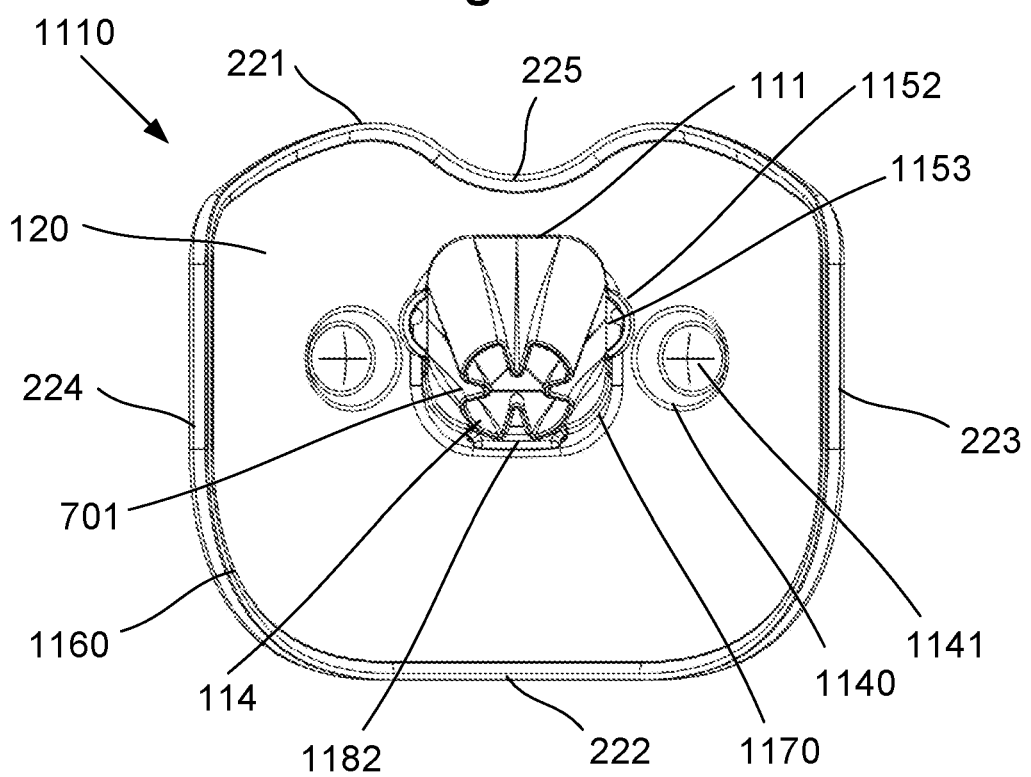

Another example of a shielded intubation guide 1110 is shown in FIGS. 11A to 11C. The shielded intubation guide 1110 includes a separate removable cap-seal part 1030 as per the previous example of the shielded intubation guide 1010 shown in FIG. 10, but in this case, the shielded intubation guide 1110 also includes a number of additional optional features incorporated into the shield 120 and body 111.

In this example, the shielded intubation guide 1110 include different types of additional openings through the shield 120, separate from the main passageway 112, for facilitating access to the subject's oral cavity for various purposes. In this particular example, the shielded intubation guide 1110 includes a pair of suction ports 1140 and a pair of drainage conduits 1150 arranged on either side of the proximal opening 114.

The suction ports 1140 may be provided to facilitate suction of fluids such as saliva, blood or vomit before or during intubation. Each suction port 1140 provides an aperture through the shield 120, through which a suction tube or other suitable suction device can be inserted to allow suction of fluids from the subject's oral cavity. In this example, the aperture of each suction port 1140 is defined at an angle relative to the shield 120, so that the suction tube or suction device will be directed towards the body 111 as it is inserted through the suction port 1140. As a result, the suction tube or suction device may follow the side wall of the body towards the pharynx of the subject as it is inserted through the suction port 1140, which can assist proper positioning of the tip of the suction tube/device in use.

In this example, the suction ports 1140 may also include port seals 1141 for closing the suction port apertures. The port seals 1141 will preferably function in a similar manner as described above for the seals 601, 1032 in previous examples, but will be configured to permit insertion of the suction tube/device in use (as opposed to the blade portion 142 of the intubation device 140). Thus, it will be appreciated that each port seal 1141 may be configured so that the port seal 1141 is normally in a closed position for sealing the suction port 1140 and is moveable to an open position when the suction tube/device is inserted through the suction port 1140. Preferably, the port seal 1141 may be configured to form a partial seal surrounding the suction tube/device in use. It will be understood that the port seals 1141 may help to reduce emissions from the subject's mouth that could otherwise escape from the suction ports 1140.

The embodiment of the shielded intubation guide 1110 shown in FIGS. 11A to 11C additionally includes drainage conduits 1150 arranged on either side of the proximal opening 113 (which is covered by the cap-seal 1030 in this example). The drainage conduits are provided to allow drainage of fluids, including air with suspended droplets or aerosols from the subject's oral cavity.

As can be seen in the front view of the shielded intubation guide 1110 in FIG. 11A, each drainage conduit 1150 extends along the shield 120 from a respective conduit aperture through the shield 120 located adjacent to the proximal opening 113 (which is covered by the cap-seal 1030 in this example) to a proximal conduit opening 1151 near a lateral edge 223, 224 of the shield 120. Turning to the rear views of the shielded intubation guide 1110 in FIGS. 11B and 11C, each drainage conduit 1150 includes an conduit body portion 1152 that extends partially along the body 111 in a parallel arrangement, and which provides a distal conduit opening 1153 that will be positioned inside the subject's oral cavity when the body 111 of the shielded intubation guide 1110 is inserted into the subject's mouth.

It will be appreciated that, when the subject is lying down on a bed, operating table or the like, the proximal conduit openings 1151 of the drainage conduits 1150 will face down towards both lateral edges of the shield 120, and the distal conduit openings 1153 will face towards the pharynx on respective lateral sides of the body 111 and its internal passageway 112, inside the subject's mouth. A catheter or tubing may be connected to the proximal openings 1151 of the drainage conduits 1150, with its other end connected to a suction source or other form of airflow, with a viral/bacterial filter for capturing any microorganisms, to thereby allow drainage via the drainage conduits 11150 without exposing the user to any emissions of fluid, droplets or aerosols. The diameter of the proximal conduit opening 1151 should be standard for connection with standard tubing. However, if a suction catheter on suction or airflow is not added, still the outflow of aerosols (if any) will be directed towards the floor (instead of towards the user). The proximal conduit openings 1151 may be closed with respective conduit caps (not shown) when these are not being used for drainage, to thereby prevent emissions from escaping via the drainage conduits.

In this example, the shield 120 includes a rim 1160 that is configured to engage with a face of the subject to thereby form a seal around the mouth of the subject. In this example, the rim 1160 extends around the circumference of the shield 120, but this is not essential and in some examples the rim may be positioned inside the edges of the shield 120. The rim 1160 may be provided with a foam or inflatable cuff as in common ventilation masks, for providing an enhanced sealing effect. It will be appreciated that the rim 1160 can further reduce emissions from the subject's mouth, both before and during an endotracheal intubation procedure.

In this particular embodiment, the body 111 includes a thickened region 1170 surrounding the body 111 near the shield. This thickened region 1170 can help to protect the subject's teeth from the blade portion 142 of the intubation device 140 during its insertion, and can also help to protect the body 111 from damage if the subject bites down with their teeth. The body 111 may additionally include dental protrusions 1181, 1182, which protrude outwardly from the body 111 and are offset from the shield 120. The dental protrusions 1181, 1182 are provided to engage with inside surfaces of the teeth of the subject in use to thereby help to secure the shielded intubation guide 1110 inside the mouth after the body 111 has been inserted.

Figure 12:
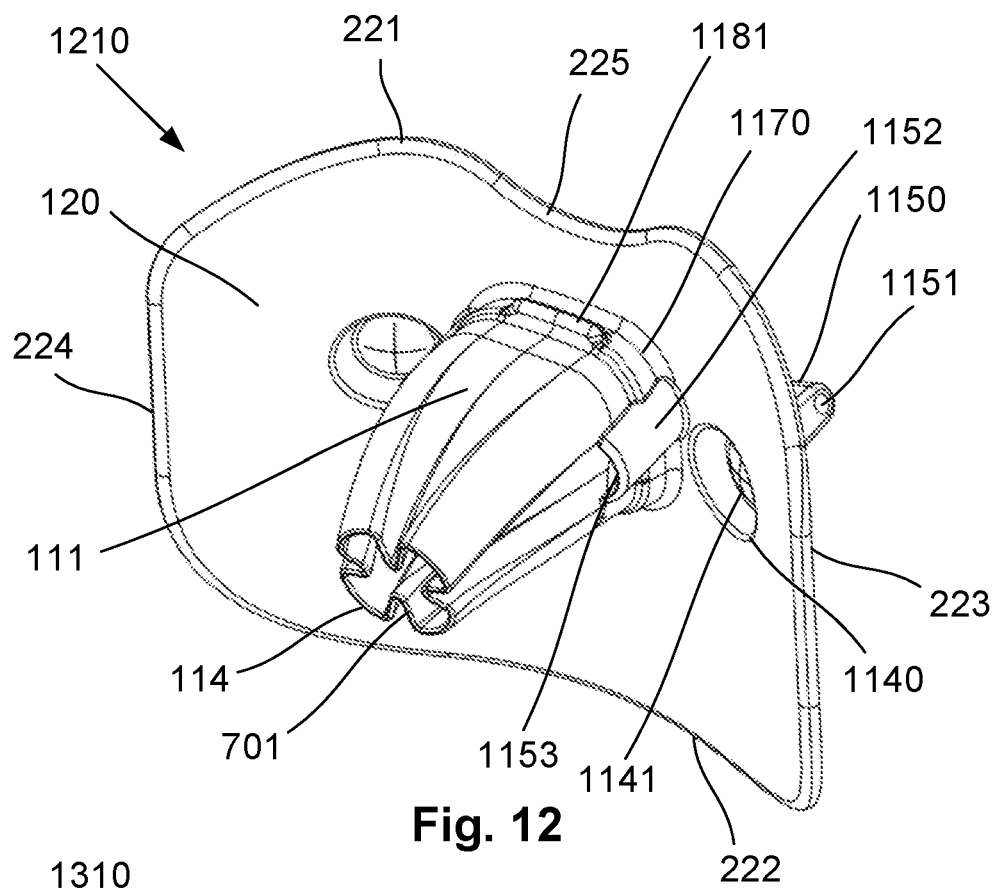
FIG. 12 is a perspective view of a ninth example of a shielded intubation guide, illustrating an example of a short body configuration.
Figure 13:
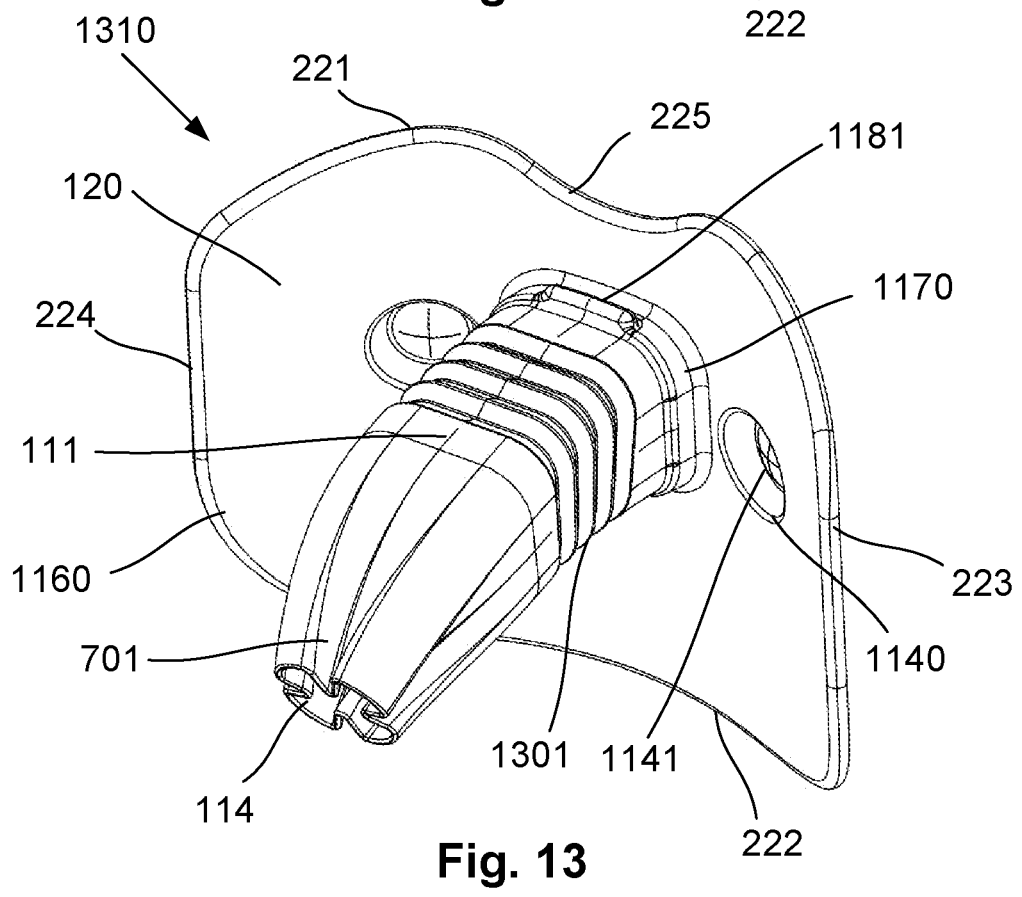
FIG. 13 is a perspective view of a tenth example of a shielded intubation guide, illustrating an example of a longitudinally extendable body.

FIGS. 12 and 13 illustrate further examples of embodiments of shielded intubation guides, illustrating some potential variations to the design of the body 111, as discussed below.

FIG. 12 shows an example of a shielded intubation guide 1210, having a relatively short body configuration compared to previous examples. In this case, the length of the body 111 is selected so that the distal opening 114 will be positioned in the oral cavity of the subject, specifically between the tongue and the palate of the subject, when the shielded intubation guide 1210 is inserted into the mouth of the subject. This short body configuration can help to avoids cough or gag reflexes before any endotracheal intubation and particularly while performing an endotracheal intubation on an awake subject.

FIG. 13 shows another example of a shielded intubation guide 1310, having a longitudinally expandable body 111. In this example, the body includes a longitudinally expandable region 1301 that extends circumferentially around the body 111 and allows the body 111 to expand longitudinally in use. The shielded intubation guide 1310 may be provided with the longitudinally expandable region 1301 in a normally collapsed state so that the body 111 is initially in a relatively short configuration for insertion into the mouth of the subject.

When the shielded intubation guide 1310 is inserted into the subject's mouth, the distal opening 114 may be positioned in in the oral cavity of the subject, specifically between the tongue and the palate of the subject. Then, when the blade portion 142 of the intubation device 140 is introduced into the passageway 112, the longitudinally expandable region 1301 will expand to thereby expand the body 111 longitudinally.

It will be appreciated that this will result in effectively lengthening the body 111, such that the distal opening 114 may be moved to a position deeper into the subject's airway, such as beyond the subject's tongue and palate inside the pharynx. The specific positioning of the distal opening 114 in use will of course depend on the configuration of the shielded intubation guide 1310, and particularly the body 111 and the longitudinally expandable region 1301. In any event, the extended length of the body 111 will assist in directing the endotracheal tube during the endotracheal intubation procedure.

As can be seen in FIG. 13, the longitudinally expandable region 1301 can be provided in a construction resembling an accordion and will preferably be formed from a relatively flexible material and/or have a relatively reduced thickness to facilitate the expandability. However, it will be appreciated that alternative construction techniques may be used to provide the longitudinally expandable region 1301. For instance, a suitable longitudinally expandable region 1301 may be provided using telescoping body portions.

In any event, the capability for expanding the body 111 longitudinally will allow the shielded intubation guide 1310 to be used in a continuum from awake subjects to paralysed subjects, noting that the use of a shielded intubation guide having a relatively longer fixed body length in a non-paralysed subject may risk provoking a cough or gag reflex.

In the present example, the insertion of the blade portion 142 into the passageway 112 will cause the longitudinally expandable region 1301 to expand, since the configuration of the other, circumferentially expanding expandable regions 701 near the distal opening 114 will form a relatively close fit around the blade portion 142 that will result in the blade portion 142 applying pressure to the distal end of the body 111 to thereby cause the normally collapsed longitudinally expandable region 1301 to expand. It will be appreciated that this will require the respective expandable regions 701, 1301 to be configured so that the longitudinally expandable region 1301 expands before the circumferentially expanding expandable regions 701 expand to allow the blade portion 142 to pass through the distal opening 114. It will be appreciated that the expansion may alternatively be caused by an externally activated expanding mechanism or the like.

Figure 14A:
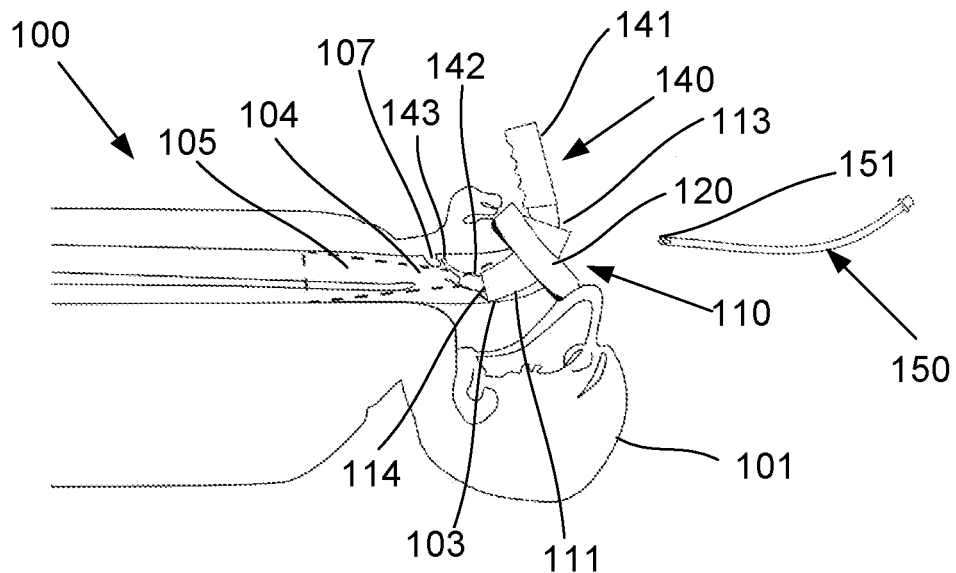
FIGS. 14A and 14B are cross section views showing steps of manually advancing an endotracheal tube using a conventional laryngoscope with the first example of the shielded intubation guide.
Figure 14B:
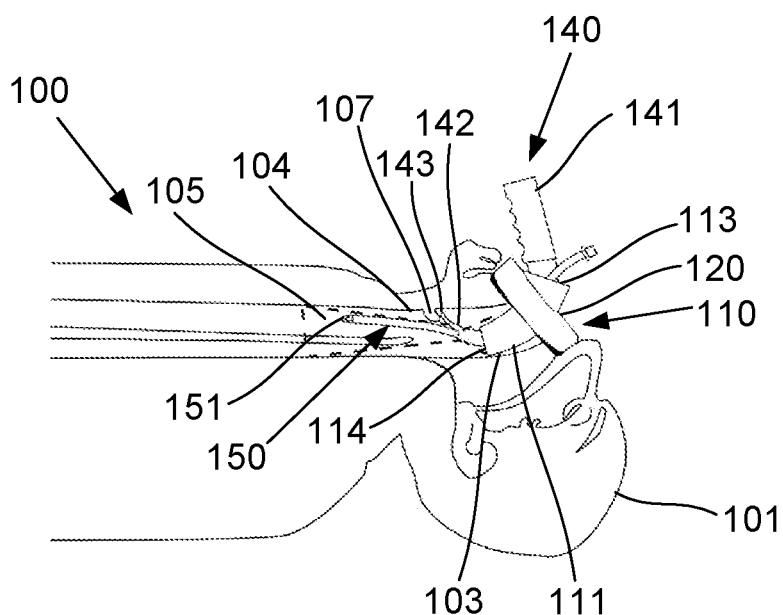

FIGS. 14A and 14B are cross section views showing steps of manually advancing an endotracheal tube using a conventional laryngoscope with the first example of the shielded intubation guide 110. It should be appreciated that the steps depicted in FIGS. 14A and 14B effectively replace the steps depicted in FIGS. 1E and 1F of the method described with reference to FIGS. 1A to 1H, but using a conventional laryngoscope as the intubation device 140 instead of the single handed version of the intubation device shown previously. It will be appreciated that the conventional laryngoscope in this example may be either a direct vision or video laryngoscope.

It is assumed that the blade portion 142 of the intubation device 140 has been inserted into the into the passageway 112 of the shielded intubation guide 110 generally as per FIG. 1D, and the light source may be activated during insertion as discussed previously. But, with regard to FIG. 14A, in this case the endotracheal tube 150 is provided separately from the intubation device 140. Turning to FIG. 14B, the endotracheal tube 150 is manually advanced along the blade portion 142 of the intubation device 140 and through the passageway 112, to introduce the tip 151 of the endotracheal tube 150 into the trachea 105 of the subject. Then the rest of the method can continue generally as previously described above with reference to FIGS. 1G to 1H.

It will be understood that, when a conventional laryngoscope is used as the intubation device 140 in this manner, the user will typically use one hand to hold the handle 141 of the intubation device 140 and another hand to manually advance the endotracheal tube 150.

In any event, it will be appreciated that the above described different embodiments of the shielded intubation guide can allow endotracheal intubation to be performed, whilst substantially reducing emissions from the mouth throughout the procedure.

Throughout this specification and claims which follow, unless the context requires otherwise, the word "comprise", and variations such as "comprises" or "comprising", will be understood to imply the inclusion of a stated integer or group of integers or steps but not the exclusion of any other integer or group of integers. As used herein and unless otherwise stated, the term "approximately" means ±20%.

It must be noted that, as used in the specification and the appended claims, the singular forms "a," "an," and "the" include plural referents unless the context clearly dictates otherwise. Thus, for example, reference to "a support" includes a plurality of supports. In this specification and in the claims that follow, reference will be made to a number of terms that shall be defined to have the following meanings unless a contrary intention is apparent.

It will of course be realised that whilst the above has been given by way of an illustrative example of this invention, all such and other modifications and variations hereto, as would be apparent to persons skilled in the art, are deemed to fall within the broad scope and ambit of this invention as is herein set forth.

The claims defining the invention are as follows:

1. A shielded intubation guide for use in an endotracheal intubation procedure, the shielded intubation guide including:
    a) an elongate body defining a passageway extending between a proximal opening and a distal opening, the passageway being configured for receiving a blade portion of an intubation device, the blade portion being a laryngoscope blade, wherein the shielded intubation guide is configured for insertion into a mouth of the subject so that the proximal opening is positioned proximate to the mouth of the subject and the distal opening is positioned in an airway of the subject and the shielded intubation guide is configured to, in use, at least one of: i) hold a tongue of the subject; and ii) depress the tongue; and
    b) a shield around the proximal opening, wherein the shield is configured to substantially cover the mouth of the subject in use to thereby substantially reduce emissions from the mouth of the subject,
    wherein the shielded intubation guide is configured to allow endotracheal intubation of the subject to be performed using an intubation device and the shielded intubation guide by:
        i) inserting the blade portion of the intubation device into the passageway of the shielded intubation guide;
        ii) positioning a distal end of the blade portion of the intubation device proximate to the larynx of the subject; and
        iii) advancing an endotracheal tube along the blade portion of the intubation device through the passageway into a trachea of the subject.

2. A shielded intubation guide according to claim 1, wherein the shield is configured to substantially reduce emissions from the mouth of the subject of one or more of:
    a) fluids;
    b) droplets;
    c) aerosols; and
    d) light emitted from a light source proximate to the distal end of the blade portion of the intubation device during a light guided endotracheal intubation procedure.

3. A shielded intubation guide according to claim 2, wherein the shield includes a flange extending outwardly from the body, the flange being configured to substantially cover the mouth of the subject in use, and wherein at least one of:
    a) the flange surrounds the proximal opening;
    b) the flange includes opposing lateral flange portions that are curved towards the distal opening;
    c) the flange includes a superior edge having a recess for aligning with a nose of the subject in use;
    d) the flange is configured to prevent over-insertion of the shielded intubation guide by abutting the subject's mouth to thereby ensure that the proximal opening remains positioned outside the mouth; and
    e) the proximal opening is at least one of:
        i) offset proximally from the flange; and
        ii) oriented at an angle relative to the flange.

4. A shielded intubation guide according to claim 1, wherein at least one of:
   a) the shielded intubation guide is configured to be broken along the passageway and along a section of the shield;
   b) the body of the shielded intubation guide includes a break line extending longitudinally along a side of the passageway and along the section of the shield, to thereby allow the shielded intubation guide to be broken along the break line; and
   c) the shielded intubation guide includes cutting marks and is configured to be cut along the passageway and along a section of the shield, by following the cutting marks.

5. A shielded intubation guide according to claim 1, wherein at least one of:
   a) a shape of the proximal opening is selected based on a cross section shape of the blade portion of the intubation device;
   b) a size of the proximal opening is selected based on a cross section size of the blade portion of the intubation device;
   c) a shape of the passageway is selected based on a cross section shape of the blade portion of the intubation device;
   d) a size of the passageway is selected based on a cross section size of the blade portion of the intubation device; and
   e) the body is curved, wherein a curvature of the body is selected based on a curvature of the blade portion of the intubation device.

6. A shielded intubation guide according to claim 1, wherein at least one of:
   a) the shielded intubation guide is formed from a flexible material;
   b) the shielded intubation guide is configured to expand when receiving the blade portion; and
   c) at least one wall of the body includes an expandable region, wherein the expandable region at least one of:
      i) extends longitudinally from the distal opening at least partially along the passageway and allows the body to expand circumferentially; and
      ii) extends circumferentially around the body and allows the body to expand longitudinally.

7. A shielded intubation guide according to claim 1, wherein the shielded intubation guide includes a seal covering the proximal opening, the seal normally being in a closed position for sealing the proximal opening and being moveable to an open position when the blade portion of the intubation device is inserted through the passageway.

8. A shielded intubation guide according to claim 7, wherein at least one of:
   a) the seal is biased towards the closed position, such that the seal returns towards the closed position when the blade portion of the intubation device is removed from the passageway; and
   b) the seal is configured to form a partial seal surrounding at least one of the blade portion of the intubation device and the endotracheal tube in use.

9. A shielded intubation guide according to claim 1, wherein the shielded intubation guide includes a removable cap for closing the proximal opening when the blade portion of the intubation device is not being inserted into the passageway of the shielded intubation guide.

10. A shielded intubation guide according to claim 9, wherein the cap includes a seal for covering the proximal opening, the seal normally being in a closed position for sealing the proximal opening and being moveable to an open position when the blade portion of the intubation device is inserted through the passageway.

11. A shielded intubation guide according to claim 1, wherein at least one of:
   a) the shielded intubation guide is configured to allow ventilation of the subject using a ventilation mask and ventilator prior to endotracheal intubation being performed;
   b) the shielded intubation guide is formed from a transparent material;
   c) the shield includes a rim that is configured to engage with a face of the subject to thereby form a seal around the mouth of the subject; and
   d) the body has a length selected so that the distal opening is positioned in one of:
      iii) proximate to an oral cavity of the subject;
      iv) proximate to a pharynx of the subject; and
      v) between a tongue and a palate of the subject.

12. A shielded intubation guide according to claim 1, wherein the shielded intubation guide is configured for use in a light guided endotracheal intubation procedure in which, after the blade portion of the intubation device is inserted into the passageway of the shielded intubation guide, light is emitted from a light source proximate to the distal end of the blade portion of the intubation device, wherein the shield is configured to substantially prevent light emitted from the light source from escaping from the mouth of the subject.

13. A shielded intubation guide according to claim 12, wherein at least one of:
   a) the shield is formed from an opaque material; and
   b) the entire shielded intubation guide is formed from an opaque material.

14. A shielded intubation guide according to claim 1, wherein the shielded intubation guide includes at least one additional opening extending through the shield for facilitating access to an oral cavity of the subject, and wherein at least one of:
   a) the shielded intubation guide includes at least one suction port extending through the shield; and
   b) the shielded intubation guide includes at least one drainage conduit extending through the shield.

15. A method for use in an endotracheal intubation procedure, the method including:
   a) inserting a shielded intubation guide into a mouth of a subject, the shielded intubation guide including:
      i) an elongate body defining a passageway extending between a proximal opening and a distal opening, the passageway being configured for receiving a blade portion of an intubation device, the blade portion being a laryngoscope blade, the proximal opening being positioned proximate to the mouth of the subject and the distal opening being positioned in an airway of the subject; and
      ii) a shield around the proximal opening, the shield being for substantially covering the mouth of the subject and thereby substantially reducing emissions from the mouth of the subject;
   b) performing endotracheal intubation of the subject using an intubation device and the shielded intubation guide by:
      i) inserting the blade portion of the intubation device into the passageway of the shielded intubation guide;
      ii) positioning a distal end of the blade portion of the intubation device proximate to the larynx of the subject;

iii) at least one of: holding a tongue of the subject; and
ii) depressing the tongue, using the shielded intubation guide; and
iv) advancing an endotracheal tube along the blade portion of the intubation device through the passageway into a trachea of the subject,
wherein the shield substantially reduces emissions from the mouth of the subject during the endotracheal intubation procedure.

16. A method according to claim 15, wherein the shield substantially reduces emissions from the mouth of the subject of one or more of:
a) fluids;
b) droplets;
c) aerosols; and
d) light emitted from a light source proximate to the distal end of the blade portion of the intubation device during a light guided endotracheal intubation procedure.

17. A method according to claim 16, wherein the shield includes a flange extending outwardly from the body, and wherein the flange substantially covers the mouth of the subject when the shielded intubation guide is inserted into the mouth of the subject.

18. A method according to claim 15, wherein the method includes performing light guided endotracheal intubation of the subject using an intubation device and the shielded intubation guide by, after inserting the blade portion of the intubation device into the passageway of the intubation guide, causing light to be emitted from a light source proximate to the distal end of the blade portion of the intubation device, wherein the shield substantially prevents light emitted from the light source from escaping from the mouth of the subject during the light guided endotracheal intubation procedure.

19. A method according to claim 15, wherein the endotracheal intubation is performed as non-direct view intubation, and wherein the intubation device includes a video camera located proximate to the tip of the blade, the method including:
a) causing images captured by the video camera to be presented to a user on a display; and
b) the user performing the endotracheal intubation of the subject with reference to the images presented on the display.

20. A method according to claim 19, wherein at least one of:
a) the display is integrated with the intubation device;
b) the display is provided in the form of goggles worn by the user; and
c) the display is surrounded by display light shielding configured so that the user can view the display whilst the display light shielding substantially prevents light emitted from the display from escaping beyond the display light shielding and the user's face.

21. A method according to claim 15, wherein the method includes, after advancing the endotracheal tube into the trachea of the subject, and while leaving the endotracheal tube in place in the trachea of the subject:
a) withdrawing the blade portion of the intubation device from the shielded intubation guide; and
b) removing the shielded intubation guide from the mouth of the subject, wherein at least one of:
i) the shielded intubation guide is configured to be broken along the passageway and along a section of the shield, the method including breaking the shielded intubation guide to allow the shielded intubation guide to be removed while the endotracheal tube remains in place; and
ii) the method includes cutting the shielded intubation guide along the passageway and along a section of the shield to allow the shielded intubation guide to be removed while the endotracheal tube remains in place.

22. A method according to claim 15, wherein the shielded intubation guide includes a seal covering the proximal opening, the seal normally being in a closed position for sealing the proximal opening and being moveable to an open position when the blade portion of the intubation device is inserted through the passageway, the method including inserting the blade portion of the intubation device into the passageway of the shielded intubation guide through the seal, the seal substantially reducing emissions from the mouth at least prior to inserting the blade.

23. A method according to claim 22, wherein the seal is biased towards the closed position, such that the seal returns towards the closed position when the blade portion of the intubation device is removed from the passageway, the seal forming a partial seal surrounding at least one of the blade portion of the intubation device and the endotracheal tube after inserting the blade.

24. A method according to claim 15, wherein the shielded intubation guide includes a removable cap for sealing the proximal opening, the method including:
a) inserting the shielded intubation guide into the mouth of a subject with the cap sealing the proximal opening, thereby substantially reducing emissions from the mouth of the subject through the proximal opening while the cap is in place; and,
b) removing the cap prior to inserting the blade portion of the intubation device into the passageway of the shielded intubation guide.

25. A method according to claim 15, wherein at least one of:
a) the shielded intubation guide includes at least one suction port extending through the shield, the method including performing suction of fluids from an oral cavity of the subject via the suction port; and
b) the shielded intubation guide includes at least one drainage conduit extending through the shield, the method including allowing fluids to drain from an oral cavity of the subject via the drainage conduit.

* * * * *